(12) United States Patent
Chen et al.

(10) Patent No.: US 7,465,742 B2
(45) Date of Patent: Dec. 16, 2008

(54) HETEROCYCLIC COMPOUNDS HAVING ANTI-HBV ACTIVITY

(76) Inventors: Huanming Chen, 12 Amorgosa, Irvine, CA (US) 92602; Robert Tam, 63 Wellington St., Irvine, CA (US) 92618; Anneke K. Raney, 2268 Bliss Cir., Oceanside, CA (US) 92056

( * ) Notice: Subject to any disclaimer, the term of this patent is extended or adjusted under 35 U.S.C. 154(b) by 52 days.

(21) Appl. No.: 11/347,145

(22) Filed: Feb. 3, 2006

(65) Prior Publication Data

US 2006/0189643 A1 Aug. 24, 2006

Related U.S. Application Data

(60) Provisional application No. 60/652,308, filed on Feb. 11, 2005.

(51) Int. Cl.
*A61K 31/4365* (2006.01)
*C07D 495/14* (2006.01)

(52) U.S. Cl. .............. 514/293; 546/83; 546/80; 546/62; 544/126; 544/333; 544/361; 514/291; 514/285; 514/256; 514/253; 514/232.8

(58) Field of Classification Search ............. 514/293, 514/291, 285, 256, 253, 232.8; 546/83, 80, 546/62; 544/126, 333, 361
See application file for complete search history.

(56) References Cited

U.S. PATENT DOCUMENTS 6,964,956 B2 * 11/2005 Cywin et al. ........... 514/211.15

* cited by examiner

*Primary Examiner*—Charanjit S. Aulakh
(74) *Attorney, Agent, or Firm*—McDermott Will & Emery LLP

(57) ABSTRACT

This application relates to novel fused tricyclic thienopyridines of Formulas I and II, which useful for treating Hepatitis B infection and other diseases.

This application also relates to pharmaceutical compositions comprising thienopyridines and to the use of such compositions to treat Hepatitis B and other diseases.

28 Claims, No Drawings

HETEROCYCLIC COMPOUNDS HAVING ANTI-HBV ACTIVITY

CROSS REFERENCE TO RELATED APPLICATIONS

This application claims the benefit of U.S. Provisional Application No. 60/652,308, filed Feb. 11, 2005, which is hereby incorporated herein by reference.

FIELD OF THE INVENTION

This application concerns novel fused tricyclic thienopyridines which are useful for treating hepatitis B infection and other diseases.

BACKGROUND OF THE INVENTION

Hepatitis B virus (HBV) causes acute or chronic hepatitis, which may progress to liver cirrhosis and liver cancer. HBV is a DNA virus which replicates via an RNA intermediate and utilizes reverse transcription in its replication strategy [Summers and Mason, Cell 29; 403-415, 1982]. HBV DNA polymerase is responsible for the reverse transcription and has been considered the main target for anti-HBV intervention. Many nucleoside or nucleotides analogs have been discovered to be effective anti-viral agents. Examples of nucleoside analogs which have been tested are penciclovir and its oral form (FCV) [Vere Hodge, Antiviral Chem Chemother. 4: 67-84, 1993; Kruger et al., Hepatology 22: 219A, 1994; Main et al., J. Viral Hepatitis 3: 211-215, 1996], and Lamivudine [(−)-B-2'-deoxy-3'-thiacytidine]; (3TC or LMV) [Severini et al., Antimicrobial Agents Chemother. 39: 430-435, 1995; Dienstag et al., New England J Med 333: 1657-1661, 1995]. New nucleoside or nucleotide analogs that have progressed to clinical trials or are approved for HBV by FDA include Emtricitabine (FTC), Clevudine (L-FMAU), Entecavir (BMS-200, 475; ETV), diaminopurine dioxolane (DAPD), adefovir dipivoxil. (9-(2-((bis((pivaloyloxy)methoxy)phosphinyl)methoxy)-ethyl)adenine). Additionally, for a number of years interferon alpha also has been widely used for the treatment of chronic HBV infection.

Although these agents are highly effective in inhibiting HBV DNA synthesis, resistant mutants of HBV have emerged during long term nucleoside or nucleotide antiviral chemotherapy. Sustained responses to HBV treatment—as evidenced by a decrease of HBV DNA in serum and by anti-HBe or HBs seroconversion—has been observed only in a relatively small patient population.

For example, for several years interferon alpha has been widely used for the treatment of chronic HBV infection. However, interferon is effective only in certain subpopulations of chronic hepatitis B patients, and even in such patients it is poorly tolerated. Similarly, lamivudine (3'-thia-2',3'-dideoxycytidine), a particularly strong inhibitor of HBV replication, is used to treat HBV infection. However, resistance to lamivudine is increasingly common and has limited its efficacy in a high proportion of patients. The most recently-approved treatment for HBV is adefovir dipivoxil (9-(2-((bis((pivaloyloxy)methoxy)phosphinyl)methoxy)ethyl)adenine). Although this nucleoside analog is active against the lamivudine-resistant viruses, its sustained viral response rate is poor (below 20%), and its maximum tolerated dose and treatment duration are often limited by nephrotoxicity.

More recent developments in HBV research have led to clinical trials for several compounds with promising antiviral activity. For example, certain nucleoside analogs have been reported to exhibit significant anti-HBV activity (e.g., 2'-fluoro-5-methyl-beta-L-arabinofuranosyluracil (Buk-wang) and 2'-deoxy-5-fluoro-3'-thiacytidine (Gilead); 2'-deoxy-L-thymidine and 2'-deoxy-L-cytidine (both Idenix)). Similarly, carbocyclic nucleoside analogs (6H-purin-6-one, 2-amino-1,9-dihydro-9-((1S,3R,4S)-4-hydroxy-3-(hydroxymethyl)-2-methylenecyclopentyl) monohydrate (Bristol-Myers Squibb), as well as acyclic nucleoside analogs with liver targeting properties (Remofovir; Ribapharm), were reported as having anti-HBV activity in clinical trials.).

However, while most of the recently discovered drugs with anti-HBV activity exhibited promising in vitro antiviral activity, low response rates and the emergence of resistance limit the efficacy of these clinical candidates. Therefore, although various compositions and methods for HBV treatment are known in the art, there is still a need to provide new and improved compositions and methods for treatment of HBV infections in human patients.

Thus, in light of the limited efficacy, resistance profiles, and toxicity of current anti-HBV drugs, there is a strong need for novel anti-HBV drugs that are more effective and less toxic and that exhibit a different resistance profile.

Therefore, it is an object of the present invention to provide a compounds and methods for the treatment of HBV infection. Such compounds and methods also have potential for the treatment of other conditions associated with dysregulated protein kinase activity, such as inflammation and neoplastic disease.

The NF-κB pathway plays a complex role in an antiviral immune response. Nuclear factor-κB (NF-κB) is a ubiquitously expressed transcription factor that is essential to the regulation of such cellular functions as apoptosis, proliferation, and differentiation [Ghosh et al., Annu. Rev. Immunol. 16:225, 1998]. NF-κB accomplishes this regulation by coordinating the expression of genes responsible for protecting an organism after physical, chemical, and/or microbial damage. Thus, NF-κB has an inherent role in the induction of an immune response and concomitant inflammation. [Baeuerle and Baltimore. Cell 87:13, 1996]. The activity of NF-κB can be modulated by viral proteins. (Bose et al., PNAS 100, 2003; Purcell et al., Am. J. Physiol. Gastrointest. Liver Physiol. 280, 2001). Such effects can be both interferon-dependent and interferon-independent (Pfeffer et al., J. Biol. Chem. 279:30, 31304-31311, 2004).

The NF-κB family of transcription factors includes a set of structurally related and evolutionarily conserved DNA binding proteins (Baldwin, Annu. Rev. Immunol. 14:649, 1996). NF-κB contains a nuclear localization sequence (NLS) that directs the protein to the nucleus to carry out its role in genetic regulation. However, under normal conditions NF-κB is sequestered in the cytoplasm because the NLS is masked by tightly bound inhibitory proteins; these inhibitors of NF-κB are known as IκB (Beg and Baldwin, Genes Dev. 7:2064, 1993; Thompson et al., Cell 80:573, 1995; Whiteside et al., EMBO J. 16:1413, 1997). Activators of NF-κB act by inactivating IκB, via the mechanisms of phosphorylation, ubiquitination, and degradation. Thus, the elimination of IκB exposes the NLS allowing NF-κB to translocate to the nucleus to activate specific target genes.

The signal responsible for inactivation of IκB is typically a cellular response to an extracellular stimulus (Tumor Necrosis Factor α (TNFα), Interleukin-1β (IL-1β), lipopolysaccharide (LPS)) or to chemical and physical stress. The signal originates at a cell surface receptor, such as the TNF-receptor or IL-1 receptor; the signal is internalized and transduced through the cell via a cascade of phosphorylation events. Each receptor binds unique adapter molecules specific to the receptor and stimulus and in turn activates downstream kinases including NF-κB interacting kinase (NIK), MAPK/extracellular signal-regulated kinase kinase-1 (MEKK-1), and IκB kinases α and β (IKKα/β). IKKβ is responsible for liberating NF-κB by phosphorylating the inhibitory subunit IκBα.

Phosphorylation of IκBα by IKKΟ triggers ubiquitin ligase (Skp1/Cul 1/F-box protein FWD1) to ubiquitinate IκBα and target it for degradation via the 26S proteasome [Yaron et al., Nature 396:590, 1998; Winston et al., Genes Dev. 13:270, 1999; Spencer et al., Genes Dev. 13:284, 1999].

The IκB kinases (TKKα and IKKβ) are serine-threonine protein kinases. They belong to a large multi-protein complex, called the "signalsome" [Mercurio et al., Science 278: 860, 1997; Woronicz et al., Science 278:866, 1997; Zandi et al., 91:243, 1997]. The signalsome is the machinery responsible for transducing the stimulus that results in NF-κB activation. The genes that encode the signalsome components have been cloned, expressed, and reconstituted in vitro to demonstrate activation of NF-κB via IκB phosphorylation [Régnier et al., Cell 90:373, 1997; DiDonato et al., Nature 388:548, 1997; Zandi et al., Cell 91:243, 1997; Woronicz et al., Science 278: 866, 1997; Mercurio et al., Science 278:860, 1997; Cohen et al., Nature 395:292, 1998]. IKK family members share homologous amino-terminal kinase domains that are activated by NIK. In turn, IKK specifically phosphorylates IκBα and IκBβ on regulatory serine residues. Genetic studies with IKK knock-out mice point to an essential role for IKKβ in transmission of inflammatory signals, whereas IKKα is involved in developmental processes requiring NF-κB activation [Takeda et al., Science 284:313, 1999; Hu et al., Science 284:316, 1999; Li et al., Science 284:321, 1999]. Embryonic fibroblasts isolated from IKKβ-deficient mice show defects in TNFα- and IL-1-induced degradation of IκB. Furthermore, inhibition of pro-inflammatory cytokine-induced IκB degradation is not observed in cells derived from IKKα-deficient mice, suggesting that IKKβ controls the NF-κB activation rather than IKKα [Takeda et al., Science 284: 313, 1999]. Moreover, a catalytically inactive mutant of IKKβ has been shown to inhibit inflammation via activation of NF-κB through TNFα, IL-1β, LPS, and anti-CD3/anti-CD28 stimulation [O'Connell et al., J. Biol. Chem. 273:30410, 1998; Woronicz et al., Science 278:866, 1997; Zandi et al., Cell 91:243, 1997.]. Thus, IKKβ is considered by the inventors to be a validated target for therapeutic interference in a variety of pathological situations, including chronic inflammatory and autoimmune diseases, viral infection, and cancer.

Some inhibitors of IKKβ have previously been reported. WO 03/103661, WO 01/58890, and WO 03/037886 describe substituted thienopyridines and heteroaromatic carboxamide derivatives as inhibitors of IKKβ. WO 01/68648 describes substituted β-carbolines having IKKβ inhibiting activity. Substituted indoles with IKKβ inhibitory activity are reported in WO 01/30774, and substituted benzimidazoles with NK-κB inhibitory activity are described in WO 01/00610. Recently, a number of imidazoloquinoxalines and related compounds have been reported to have IKK-inhibiting activity and to be useful in treating arthritis, transplant rejection, inflammatory bowel disease, and pulmonary inflammation disease in U.S. Pub. No. 2003/0022898. Additionally, aspirin and other salicylates have been reported to bind to and inhibit IKKβ (M. Yin et al., Nature, 1998, 396, 77).

Substituted thienopyridines that inhibit cell adhesion are reported in U.S. 2001/0020030 and in A. O. Stewart et al., J. Med. Chem., 2001, 44, 988. Thienopyridines with activity as antagonists of gonadotropin releasing hormone are reported in U.S. Pat. No. 6,313,301. Substituted thienopyridines described as telomerase inhibitors are disclosed in U.S. Pat. No. 5,656,638.

BRIEF DESCRIPTION OF THE INVENTION

The present invention comprises fused tricyclic thienopyridine compounds of Formulas I and II below, which are potentially useful in treating HBV infection, as well as methods of treatment of HBV infection utilizing compounds of Formulas I and II and other fused tricyclic thienopyridines.

The present inventors have discovered that such fused tricyclic thienopyridines are effective as IKKβ inhibitors. Such compounds may be used for treatment of HBV, as well as other diseases that are directly or indirectly associated with a dysregulated kinase.

In one embodiment the present invention provides a compound of compound of Formula I below,

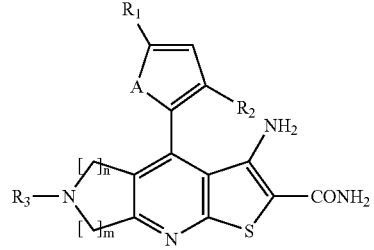

Formula I in which A is S, O, or N(CH$_3$); R$_1$ and R$_2$ are, independently, H, CH$_3$, CF$_3$, or CH$_3$O; R$_3$ is H; or R$_3$ is a 5- or 6-membered ring, said ring optionally containing one or more double bonds, optionally containing 1-3 ring heteroatoms independently selected from O, N, and S, and optionally substituted with one or two groups independently selected from CH$_3$, OCH$_3$, CO$_2$CH$_3$, OC(O)CH$_3$, CN, and halo, wherein all methyl groups are optionally substituted with 1, 2, or 3 halogen atoms; or R$_3$ is C$_{1-6}$ alkyl, C$_{1-6}$ alkanoyl, C$_{1-6}$ alkenyl, C$_{1-6}$ alkoxy, C$_{1-6}$ alkenoxy, wherein said alkyl groups, the alkyl moieties of said alkanoyl and said alkoxy groups, said alkenyl groups, and the alkenyl moieties of said alkenoxy groups may be straight-chain, branched, or cyclic, and can all optionally be substituted as follows:

a) with one, two, or three halogen atoms;
b) with one or two substituents independently selected from hydroxy, carboxyl, cyano, benzyl, benzoyl, and benzoyloxy;
c) with one saturated, unsaturated, or aromatic 5- or 6-membered ring containing 0-3 heteroatoms selected from N, O, and S, said ring optionally substituted with one or two groups independently selected from CH$_3$, OCH$_3$, C(O)CH$_3$, CO$_2$CH$_3$, OC(O)CH$_3$, CN, and halo, wherein all methyl groups are optionally substituted with 1, 2, or 3 halogen atoms; and
d) with one group selected from C$_{1-6}$ alkanoyl, C$_{1-6}$ alkoxycarbonyl, C$_{1-6}$ alkylcarbamoyl, ethylcarbamoylmethyl methylcarbamoylmethyl, 2-hydroxy-2-phenyl-ethylcarbamoylmethyl, or N-phthalimido;

or R$_3$ is R$_4$NHC(O), R$_4$NHC(S), or R$_4$NHCH$_2$C(O), wherein R$_4$ is C$_{1-6}$ alkyl, wherein said alkyl group may be straight-chain, branched, or cyclic, and is optionally substituted as described for R$_3$ alkyl groups, or R$_4$ is a five- or 6-membered aromatic ring containing 0-3 heteroatoms independently selected from O, N, and S, all R$_4$ optionally substituted with one or two substituents independently selected from halo, methyl, and benzyl, wherein all rings are optionally substituted with one or two groups independently selected from CH$_3$, OCH$_3$, CO$_2$CH$_3$, OC(O)CH$_3$, CN, and halo, wherein all methyl groups are optionally substituted with 1, 2, or 3 halogen atoms; and m and n are, independently, 1 or 2, provided that m and n are not both 2; and further provided that when n=1, m=2, and $R_1$ and $R_2$ are both H, then $R_3$ is not methyl.

In a more particular embodiment, the present invention provides a compound of Formula I above, wherein A is S, n is 1, m is 1, $R_1$ is H, and $R_2$ is H or $CH_3$.

In another particular embodiment, this invention provides a compound of Formula I above, in which A is S, n is 1, m is 1, $R_1$ is H, $R_2$ is H or $CH_3$, and $R_3$ is H or $C_{1-6}$ alkyl, optionally substituted with one or two substituents independently selected from halo, hydroxy, cyano, phenyl, pyridyl, benzoyl, benzoyl methyl, benzoyloxy, $C_{1-6}$ alkoxycarbonyl, $C_{1-6}$ alkylcarbamoyl, N-phthalimido, or $R_3$ is a 5- or 6-membered aromatic ring containing 1-3 heteroatoms independently selected from O, N, and S, wherein all rings are optionally substituted with one or two substituents independently selected from halo, $CH_3$, $CH_3O$, CN, $CF_3$, and $CH_3C(O)$, wherein all methyl groups are optionally substituted 1-3 chlorine atoms.

In another particular embodiment, this invention provides a compound of Formula I above, in which A is S, n is 1, m is 1, $R_1$ is H, $R_2$ is H or $CH_3$, and $R_3$ is $C_{1-4}$ alkyl, optionally monosubstituted with halogen, hydroxy, phenyl, benzyl, pyridyl, and pyridyl methyl, wherein the phenyl and pyridyl rings are optionally further monosubstituted with methyl or halogen.

In another particular embodiment, this invention provides a compound of Formula I above, in which A is S, n is 1, m is 1, $R_1$ is H, $R_2$ is H or $CH_3$, and $R_3$ is $R_4NHC(O)$, $R_4NHC(S)$, or $R_4NHCH_2C(O)$, where $R_4$ is $C_{1-6}$ alkyl, which alkyl group may be straight-chain, branched, or cyclic, and which is optionally substituted as described in previous paragraphs for $R_3$ alkyl groups, or $R_4$ is a five- or 6-membered aromatic ring containing 0-3 heteroatoms independently selected from O, N, and S, all $R_4$ optionally substituted with one or two substituents independently selected from halo, methyl, and benzyl, in which all rings are optionally substituted with one or two groups independently selected from $CH_3$, $OCH_3$, $CO_2CH_3$, $OC(O)CH_3$, CN, and halo, wherein all methyl groups are optionally substituted with 1, 2, or 3 halogen atoms.

In another embodiment, this invention provides a compound of Formula I in which A is S, n is 2, m is 1, $R_1$ is H, and $R_2$ is H or $CH_3$.

In another embodiment, this invention provides a compound of Formula I in which A is S, n is 2, m is 1, $R_1$ is H, $R_2$ is H or $CH_3$ and in which $R_3$ is H or $C_{1-4}$ alkyl.

In another embodiment, this invention provides a compound of Formula I in which A is O, n is 1, m is 1, $R_1$ is H, and $R_2$ is H or $CH_3$.

In another embodiment, this invention provides a compound of Formula I in which A is O, n is 1, m is 1, $R_1$ is H, $R_2$ is H or $CH_3$, and $R_3$ is H or $C_{1-6}$ alkyl, optionally substituted with one or two substituents independently selected from halo, hydroxy, cyano, phenyl, pyridyl, benzoyl, benzoyl methyl, benzoyloxy, $C_{1-6}$ alkoxycarbonyl, $C_{1-6}$ alkylcarbamoyl, N-phthalimido, or $R_3$ is a 5- or 6-membered aromatic ring containing 1-3 heteroatoms independently selected from O, N, and S, in which all rings are optionally substituted with one or two substituents independently selected from halo, $CH_3$, $CH_3O$, CN, $CF_3$, and $CH_3C(O)$, where all methyl groups are optionally substituted 1-3 chlorine atoms.

In another embodiment, this invention provides a compound of Formula I in which A is O, n is 1, m is 1, $R_1$ is H, $R_2$ is H or $CH_3$, and $R_3$ is $C_{1-4}$ alkyl, optionally monosubstituted with halogen, hydroxy, phenyl, benzyl, pyridyl, and pyridyl methyl, wherein the phenyl and pyridyl rings are optionally further monosubstituted with methyl or halogen.

In another embodiment, this invention provides a compound of Formula I in which A is O, n is 1, m is 1, $R_1$ is H, $R_2$ is H or $CH_3$, and $R_3$ is $R_4NHC(O)$, $R_4NHC(S)$, or $R_4NHCH_2C(O)$, where $R_4$ is $C_{1-6}$ alkyl, which alkyl group may be straight-chain, branched, or cyclic, and is optionally substituted as described for $R_3$ alkyl groups, or $R_4$ is a five- or 6-membered aromatic ring containing 0-3 heteroatoms independently selected from O, N, and S, all $R_4$ optionally substituted with one or two substituents independently selected from halo, methyl, and benzyl, wherein all rings are optionally substituted with one or two groups independently selected from $CH_3$, $OCH_3$, $CO_2CH_3$, $OC(O)CH_3$, CN, and halo, wherein all methyl groups are optionally substituted with 1, 2, or 3 halogen atoms.

In another embodiment, this invention provides a compound of Formula II below

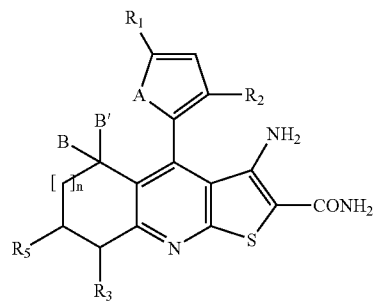

Formula II where n is zero, 1, 2, or 3; A is S, O, or $N(CH_3)$; B and B' are either both H or jointly oxo; $R_1$ and $R_2$ are, independently, H, $CH_3$, $CF_3$, or $CH_3O$; $R_3$ is H; or $R_3$ is a 5- or 6-membered ring, which optionally contains one or more double bonds and also optionally contains 1-3 ring heteroatoms independently selected from O, N, and S, which may be substituted with one or two groups independently selected from $CH_3$, $OCH_3$, $CO_2CH_3$, $OC(O)CH_3$, CN, and halo, where all methyl groups are optionally substituted with 1, 2, or 3 halogen atoms; or $R_3$ is $C_{1-6}$ alkyl, $C_{1-6}$ alkanoyl, $C_{1-6}$ alkenyl, $C_{1-6}$ alkoxy, $C_{1-6}$ alkenyoxy, wherein said alkyl groups, the alkyl moieties of said alkanoyl and said alkoxy groups, said alkenyl groups, and the alkenyl moieties of said alkenoxy groups may be straight-chain, branched, or cyclic, and may optionally be substituted as follows:

a) with one, two, or three halogen atoms;
b) with one or two substituents independently selected from hydroxy, carboxyl, cyano, benzyl, benzoyl, and benzoyloxy;
c) with one saturated, unsaturated, or aromatic 5- or 6-membered ring containing 0-3 heteroatoms selected from N, O, and S, said ring optionally substituted with one or two groups independently selected from $CH_3$, $OCH_3$, $C(O)CH_3$, $CO_2CH_3$, $OC(O)CH_3$, CN, and halo, wherein all methyl groups are optionally substituted with 1, 2, or 3 halogen atoms; and
d) with one group selected from $C_{1-6}$ alkanoyl, $C_{1-6}$ alkoxycarbonyl, $C_{1-6}$ alkylcarbamoyl, ethylcarbamoylmethyl methylcarbamoylmethyl, 2-hydroxy-2-phenyl-ethylcarbamoylmethyl, or N-phthalimido;

or $R_3$ is $R_4NHC(O)$, $R_4NHC(S)$, or $R_4NHCH_2C(O)$, wherein $R_4$ is $C_{1-6}$ alkyl, wherein said alkyl group may be straight-chain, branched, or cyclic, and is optionally substituted as described for $R_3$ alkyl groups, or $R_4$ is a five- or 6-membered aromatic ring containing 0-3 heteroatoms independently selected from O, N, and S, all $R_4$ optionally substituted with one or two substituents independently selected from halo, methyl, and benzyl, wherein all rings are optionally substituted with one or two groups independently selected from CH$_3$, OCH$_3$, CO$_2$CH$_3$, OC(O)CH$_3$, CN, and halo, wherein all methyl groups are optionally substituted with 1, 2, or 3 halogen atoms; and R$_5$ is H or C$_3$ alkyl;

or R$_3$ and R$_5$, together with the ring carbon atoms to which they are attached, form an additional fused 5- or 6-membered cycloalkyl group, provided that when A is O or S, then R$_1$, R$_2$, R$_3$, B, and B' are not all H, and further provided that when A is S and R$_1$ is CH$_3$, then R$_2$, R$_3$, B, and B' are not all H.

In another embodiment, this invention provides a compound of Formula I, as described in the previous paragraph, in which A is S, R$_5$ is H; and in which R$_3$ is selected from H, C$_{1-4}$ alkyl, C$_{1-4}$ alkenyl, or C$_{1-6}$ alkoxy, wherein said alkyl groups, the alkyl moieties of said alkoxy groups, and said alkenyl groups may be straight-chain, branched, or cyclic, and are optionally substituted with one or two substituents independently selected from halo, hydroxy, ethylcarbamoylmethyl, methylcarbamoylmethyl, 2-hydroxy-2-phenyl-ethylcarbamoylmethyl, benzoyl, benzoyloxy, and a 5- or 6-membered ring, said ring optionally containing one or more double bonds, optionally containing 1-3 ring heteroatoms independently selected from O, N, and S, and optionally substituted with, independently, one or two groups independently selected from CH$_3$, OCH$_3$, CF$_3$, and halo; and n=0, 1, or 2.

In another embodiment, the present invention provides a compound of Formula II as described above, further characterized in that n=1 or 2, and R$_3$ is hydrogen, methyl, methoxy, ethoxy or allyl.

In another embodiment, the present invention provides a method of treating an HBV infection, comprising providing in a person in need of treatment thereof a therapeutically effective concentration of a compound of Formula I,

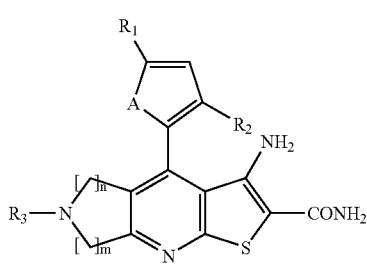

Formula I where A is S, O, or N(CH$_3$); R$_1$ and R$_2$ are, independently, H, CH$_3$, CF$_3$, or CH$_3$O; R$_3$ is H; or R$_3$ is a 5- or 6-membered ring, said ring optionally containing one or more double bonds, optionally containing 1-3 ring heteroatoms independently selected from O, N, and S, and optionally substituted with one or two groups independently selected from CH$_3$, OCH$_3$, CO$_2$CH$_3$, OC(O)CH$_3$, CN, and halo, wherein all methyl groups are optionally substituted with 1, 2, or 3 halogen atoms;

or R$_3$ is C$_{1-6}$ alkyl, C$_{1-6}$ alkanoyl, C$_{1-6}$ alkenyl, C$_{1-6}$ alkoxy, C$_{1-6}$ alkenoxy, wherein said alkyl groups, the alkyl moieties of said alkanoyl and said alkoxy groups, said alkenyl groups, and the alkenyl moieties of said alkenoxy groups may be straight-chain, branched, or cyclic, and can all optionally be substituted as follows:

a) with one, two, or three halogen atoms;
b) with one or two substituents independently selected from hydroxy, carboxyl, cyano, benzyl, benzoyl, and benzoyloxy;
c) with one saturated, unsaturated, or aromatic 5- or 6-membered ring containing 0-3 heteroatoms selected from N, O, and S, said ring optionally substituted with one or two groups independently selected from CH$_3$, OCH$_3$, C(O)CH$_3$, CO$_2$CH$_3$, OC(O)CH$_3$, CN, and halo, wherein all methyl groups are optionally substituted with 1, 2, or 3 halogen atoms; and
d) with one group selected from C$_{1-6}$ alkanoyl, C$_{1-6}$ alkoxycarbonyl, C$_{1-6}$ alkylcarbamoyl, ethylcarbamoylmethyl methylcarbamoylmethyl, 2-hydroxy-2-phenyl-ethylcarbamoylmethyl, or N-phthalimido;

or R$_3$ is R$_4$NHC(O), R$_4$NHC(S), or R$_4$NHCH$_2$C(O), wherein R$_4$ is C$_{1-6}$ alkyl, wherein said alkyl group may be straight-chain, branched, or cyclic, and is optionally substituted as described for R$_3$ alkyl groups, or R$_4$ is a five- or 6-membered aromatic ring containing 0-3 heteroatoms independently selected from O, N, and S, all R$_4$ optionally substituted with one or two substituents independently selected from halo, methyl, and benzyl, wherein all rings are optionally substituted with one or two groups independently selected from CH$_3$, OCH$_3$, CO$_2$CH$_3$, OC(O)CH$_3$, CN, and halo, wherein all methyl groups are optionally substituted with 1, 2, or 3 halogen atoms; and m and n are, independently, 1 or 2, provided that m and n are not both 2.

Another embodiment of the invention provides a method of treating an HBV infection, comprising providing in a person in need of treatment thereof a therapeutically effective concentration of a compound of Formula I above, where A is S, n is 1, m is 1, R$_1$ is H, and R$_2$ is H or CH$_3$.

Another embodiment of the invention provides a method of treating an HBV infection, comprising providing in a person in need of treatment thereof a therapeutically effective concentration of a compound of Formula I above, where A is S, n is 1, m is 1, R$_1$ is H, R$_2$ is H or CH$_3$, and where R$_3$ is H or C$_{1-6}$ alkyl, optionally substituted with one or two substituents independently selected from halo, hydroxy, cyano, phenyl, pyridyl, benzoyl, benzoyl methyl, benzoyloxy, C$_{1-6}$ alkoxycarbonyl, C$_{1-6}$ alkylcarbamoyl, N-phthalimido, or R$_3$ is a 5- or 6-membered aromatic ring containing 1-3 heteroatoms independently selected from O, N, and S, wherein all rings are optionally substituted with one or two substituents independently selected from halo, CH$_3$, CH$_3$O, CN, CF$_3$, and CH$_3$C(O), wherein all methyl groups are optionally substituted 1-3 chlorine atoms.

Another embodiment of the invention provides a method of treating an HBV infection, comprising providing in a person in need of treatment thereof a therapeutically effective concentration of a compound of Formula I above, where A is S, n is 1, m is 1, R$_1$ is H, R$_2$ is H or CH$_3$, and where R$_3$ is C$_{1-4}$ alkyl, optionally monosubstituted with halogen, hydroxy, phenyl, benzyl, pyridyl, and pyridyl methyl, wherein the phenyl and pyridyl rings are optionally further monosubstituted with methyl or halogen.

Another embodiment of the invention provides a method of treating an HBV infection, comprising providing in a person in need of treatment thereof a therapeutically effective concentration of a compound of Formula I above, where A is S, n is 1, m is 1, R$_1$ is H, R$_2$ is H or CH$_3$, and where R$_3$ is R$_4$NHC(O), R$_4$NHC(S), or R$_4$NHCH$_2$C(O), wherein R$_4$ is C$_{1-6}$ alkyl, wherein said alkyl group may be straight-chain, branched, or cyclic, and is optionally substituted as described for R$_3$ alkyl groups, or R$_4$ is a five- or 6-membered aromatic ring containing 0-3 heteroatoms independently selected from O, N, and S, all R$_4$ optionally substituted with one or two substituents independently selected from halo, methyl, and benzyl, wherein all rings are optionally substituted with one or two groups independently selected from CH$_3$, OCH$_3$, CO$_2$CH$_3$, OC(O)CH$_3$, CN, and halo, wherein all methyl groups are optionally substituted with 1, 2, or 3 halogen atoms.

Another particular embodiment of the present invention is a method treating an HBV infection, comprising providing in a person in need of treatment thereof a therapeutically effective concentration of a compound of Formula I, where A is S, n is 2, m is 1, $R_1$ is H, and $R_2$ is H or $CH_3$.

Another particular embodiment of the present invention is a method treating an HBV infection, comprising providing in a person in need of treatment thereof a therapeutically effective concentration of a compound of Formula I, where A is S, n is 2, m is 1, $R_1$ is H, and $R_2$ is H or $CH_3$, wherein $R_3$ is H or $C_{1-4}$ alkyl.

Another particular embodiment of the present invention is a method treating an HBV infection, comprising providing in a person in need of treatment thereof a therapeutically effective concentration of a compound of Formula I, where A is O, n is 1, m is 1, $R_1$ is H, and $R_2$ is H or $CH_3$.

Another particular embodiment of the present invention is a method treating an HBV infection, comprising providing in a person in need of treatment thereof a therapeutically effective concentration of a compound of Formula I, where A is O, n is 1, m is 1, $R_1$ is H, $R_2$ is H or $CH_3$, and $R_3$ is H or $C_{1-6}$ alkyl, optionally substituted with one or two substituents independently selected from halo, hydroxy, cyano, phenyl, pyridyl, benzoyl, benzoyl methyl, benzoyloxy, $C_{1-6}$ alkoxycarbonyl, $C_{1-6}$ alkylcarbamoyl, N-phthalimido, or $R_3$ is a 5- or 6-membered aromatic ring containing 1-3 heteroatoms independently selected from O, N, and S, wherein all rings are optionally substituted with one or two substituents independently selected from halo, $CH_3$, $CH_3O$, CN, $CF_3$, and $CH_3C(O)$, wherein all methyl groups are optionally substituted 1-3 chlorine atoms.

Another particular embodiment of the present invention is a method treating an HBV infection, comprising providing in a person in need of treatment thereof a therapeutically effective concentration of a compound of Formula I, where A is O, n is 1, m is 1, $R_1$ is H, $R_2$ is H or $CH_3$, and $R_3$ is $C_{1-4}$ alkyl, optionally monosubstituted with halogen, hydroxy, phenyl, benzyl, pyridyl, and pyridyl methyl, wherein the phenyl and pyridyl rings are optionally monosubstituted with methyl or halogen.

Another particular embodiment of the present invention is a method treating an HBV infection, comprising providing in a person in need of treatment thereof a therapeutically effective concentration of a compound of Formula I, where A is O, n is 1, m is 1, $R_1$ is H, $R_2$ is H or $CH_3$, and $R_3$ is $R_4NHC(O)$, $R_4NHC(S)$, or $R_4NHCH_2C(O)$, wherein $R_4$ is $C_{1-6}$ alkyl, wherein said alkyl group may be straight-chain, branched, or cyclic, and is optionally substituted as described for $R_3$ alkyl groups, or $R_4$ is a five- or 6-membered aromatic ring containing 0-3 heteroatoms independently selected from O, N, and S, all $R_4$ optionally substituted with one or two substituents independently selected from halo, methyl, and benzyl, wherein all rings are optionally substituted with one or two groups independently selected from $CH_3$, $OCH_3$, $CO_2CH_3$, $OC(O)CH_3$, CN, and halo, wherein all methyl groups are optionally substituted with 1, 2, or 3 halogen atoms.

Another particular embodiment of the present invention is a method treating an HBV infection, comprising providing in a person in need of treatment thereof a therapeutically effective concentration of a compound of Formula II

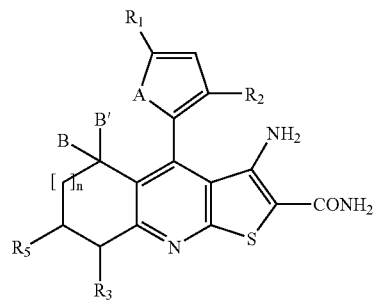

Formula II wherein n is zero, 1, 2, or 3; A is S, O, or $N(CH_3)$;

B and B' are either both H or jointly oxo;

$R_1$ and $R_2$ are, independently, H, $CH_3$, $CF_3$, or $CH_3O$;

$R_3$ is H;

or $R_3$ is a 5- or 6-membered ring, said ring optionally containing one or more double bonds, optionally containing 1-3 ring heteroatoms independently selected from O, N, and S, and optionally substituted with one or two groups independently selected from $CH_3$, $OCH_3$, $CO_2CH_3$, $OC(O)CH_3$, CN, and halo, wherein all methyl groups are optionally substituted with 1, 2, or 3 halogen atoms;

or $R_3$ is $C_{1-6}$ alkyl, $C_{1-6}$ alkanoyl, $C_{1-6}$ alkenyl, $C_{1-6}$ alkoxy, $C_{1-6}$ alkenoxy, wherein said alkyl groups, the alkyl moieties of said alkanoyl and said alkoxy groups, said alkenyl groups, and the alkenyl moieties of said alkenoxy groups may be straight-chain, branched, or cyclic, and may optionally be substituted as follows:

a) with one, two, or three halogen atoms;

b) with one or two substituents independently selected from hydroxy, carboxyl, cyano, benzyl, benzoyl, and benzoyloxy;

c) with one saturated, unsaturated, or aromatic 5- or 6-membered ring containing 0-3 heteroatoms selected from N, O, and S, said ring optionally substituted with one or two groups independently selected from $CH_3$, $OCH_3$, $C(O)CH_3$, $CO_2CH_3$, $OC(O)CH_3$, CN, and halo, wherein all methyl groups are optionally substituted with 1, 2, or 3 halogen atoms; and d) with one group selected from $C_{1-6}$ alkanoyl, $C_{1-6}$ alkoxycarbonyl, $C_{1-6}$ alkylcarbamoyl, ethylcarbamoylmethyl methylcarbamoylmethyl, 2-hydroxy-2-phenyl-ethylcarbamoylmethyl, or N-phthalimido;

or $R_3$ is $R_4NHC(O)$, $R_4NHC(S)$, or $R_4NHCH_2C(O)$, wherein $R_4$ is $C_{1-6}$ alkyl, wherein said alkyl group may be straight-chain, branched, or cyclic, and is optionally substituted as described for $R_3$ alkyl groups, or $R_4$ is a five- or 6-membered aromatic ring containing 0-3 heteroatoms independently selected from O, N, and S, all $R_4$ optionally substituted with one or two substituents independently selected from halo, methyl, and benzyl, wherein all rings are optionally substituted with one or two groups independently selected from $CH_3$, $OCH_3$, $CO_2CH_3$, $OC(O)CH_3$, CN, and halo, wherein all methyl groups are optionally substituted with 1, 2, or 3 halogen atoms; and $R_5$ is H or $C_3$ alkyl; or $R_3$ and $R_5$, together with the ring carbon atoms to which they are attached, form an additional fused 5- or 6-membered cycloalkyl group.

In another embodiment, this invention provides a method as described in the previous paragraph, where A is S, $R_5$ is H; and where $R_3$ is selected from H, $C_{1-4}$ alkyl, $C_{1-4}$ alkenyl, or $C_{1-6}$ alkoxy, wherein said alkyl groups, the alkyl moieties of said alkoxy groups, and said alkenyl groups may be straight-chain, branched, or cyclic, and are optionally substituted with one or two substituents independently selected from halo, hydroxy, ethylcarbamoylmethyl, methylcarbamoylmethyl, 2-hydroxy-2-phenyl-ethylcarbamoylmethyl, benzoyl, benzoyloxy, and a 5- or 6-membered ring, said ring optionally containing one or more double bonds, optionally containing 1-3 ring heteroatoms independently selected from O, N, and S, and optionally substituted with, independently, one or two groups independently selected from $CH_3$, $OCH_3$, $CF_3$, and halo; and n=0, 1, or 2.

In another embodiment, this invention provides a method treating an HBV infection, comprising providing in a person in need of treatment thereof a therapeutically effective concentration of a compound of Formula II above, wherein n is 1 or 2, A is S, O, or $N(CH_3)$; B and B' are either both H or jointly oxo; $R_1$ and $R_2$ are, independently, H, $CH_3$, $CF_3$, or $CH_3O$; and $R_3$ is H, methyl, methoxy, ethoxy or allyl.

DETAILED DESCRIPTION OF THE INVENTION

The term "alkyl," as used herein, refers to a straight-chain or branched saturated group with 1-20 carbon atoms, derived from an alkane by the removal of one hydrogen atom.

The term "alkenyl," as used herein, refers to a monovalent straight-chain or branched group of 2-12 carbon atoms containing at least one carbon-carbon double bond, derived from an alkene by the removal of one hydrogen atom.

The term "alkoxy," as used herein, refers to an alkyl group attached to the parent molecular group through an oxygen atom.

The term "amino," as used herein, refers to a $—NR_aR_b$ group, where $R_a$ and $R_b$ are independently selected from hydrogen, alkyl, aryl or heteroaryl.

The term "aminocarbonyl," as used herein, refers to an amino group, as defined herein, attached to the parent molecular moiety through a carbonyl group, as defined herein.

The term "aminocarbonyloxy," as used herein, refers to an aminocarbonyl group, as defined herein, attached to the parent molecular moiety through an oxygen atom.

The term "aryl," as used herein, refers to a carbocyclic ring system, mono-or bi-cyclic, having one or two aromatic rings. The aryl group can also be fused to a cyclohexane, cyclohexene, cyclopentane or cyclopentene ring. The aryl groups of this invention are optionally substituted.

The term "oxo," as used herein, refers to =O, and the term "carbonyl," as used herein, refers to a C=O group.

The term "cycloalkyl," as used herein, refers to a monovalent aliphatic cyclic hydrocarbon group of 3-12 carbons derived from a cycloalkane by the removal of one hydrogen atom.

The terms "halo" and "halogen," as used herein, refer to F, Cl, Br, or I.

The term "heteroaryl" represents an aryl group containing in which one, two, or three ring atoms are substituted with heteroatoms independently selected from nitrogen, oxygen, and sulfur.

The term "oxy," as used herein, refers to —O—.

The term "methylene," as used herein, refers to a —$CH_2$— group.

The term "perfluoroalkyl," as used herein, refers to an alkyl group in which all of the hydrogen atoms have been replaced by fluorine atoms.

The term "phenyl," as used herein, refers to a monocyclic carbocyclic ring system having one aromatic ring. The phenyl group can also be fused to another ring. The phenyl groups of this invention can be optionally substituted.

The term "prodrug," as used herein, represents compounds that are transformed in vivo to the parent compound of the above formula, for example, by hydrolysis in blood. A thorough discussion is provided in T. Higuchi and V. Stella, *Prodrugs as Novel Delivery Systems,* Vol. 14 of the A.C.S. Symposium Series, and in Edward B. Roche, ed., *Bioreversible Carriers in Drug Design,* American Pharmaceutical Association and Pergamon Press, 1987, both of which are incorporated herein by reference.

The terms "thioalkoxy," and "thio," as used herein, refer to an alkyl group attached to the parent molecular group through a sulfur atom.

The term "treating," as used herein, refers to reversing, alleviating, or inhibiting the progress of the disease, disorder or condition, or one or more symptoms of such disease, disorder or condition, to which such term applies. Depending on the condition of the patient, as used herein, this term also refers to preventing a disease, disorder or condition, and includes preventing the onset of a disease, disorder or condition, or preventing the symptoms associated with a disease, disorder or condition. As used herein, this term also refers to reducing the severity of a disease, disorder or condition or symptoms associated with such disease, disorder or condition prior to affliction with the disease, disorder or condition. Such prevention or reduction of the severity of a disease, disorder or condition prior to affliction refers to administration of the composition of the present invention, as described herein, to a subject that is not at the time of administration afflicted with the disease, disorder or condition. "Preventing" also refers to preventing the recurrence of a disease, disorder or condition or of one or more symptoms associated with such disease, disorder or condition. The terms "treatment" and "therapeutically," as used herein, refer to the act of treating, as "treating" is defined above.

Synthetic Methods

The compounds of this invention may be prepared by the general methods and examples presented below, and methods known to those of ordinary skill in the art. Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Reaction progress may be monitored by conventional methods such as thin layer chromatography (TLC) and mass spectrum (MS). Intermediates and products may be purified by methods known in the art, including column chromatography, high pressure liquid chromatography (HPLC), and recrystallization.

Additional abbreviations which have been used in the descriptions of the schemes and the examples that follow are: DMF for N,N-dimethylformamide, DMSO for dimethylsulfoxide, and THF for tetrahydrofuran.

As shown in Scheme I, reaction of I with one equivalent of cyanothioacetamide II in a suitable solvent such as ethanol, in the presence of a suitable base such as N-methylmorpholine produces intermediates III. Reaction of III with substituted cyclic, heterocyclic, and polycyclic ketones IV, e.g., cyclopentanones, cyclohexanones, cycloheptanones, piperidinones, pyrrolidinones, azepanones, tetrahydrofuranones, decalones, cyclohexanediones, and tetrahydropyranones, in a suitable solvent such as ethanol, in the presence of a suitable base such as N-methylmorpholine or morpholine, provides the intermediates V. Reaction of V with chloro- or bromoacetamide in a suitable solvent such as ethanol or acetone, in the presence of a suitable base such as potassium carbonate, sodium ethoxide, potassium tert-butoxide, with or without heating, provides compounds of formula VI. Substituent $R_1$ may be further modified by methods known in the art to produce additional compounds of the invention.

Scheme I

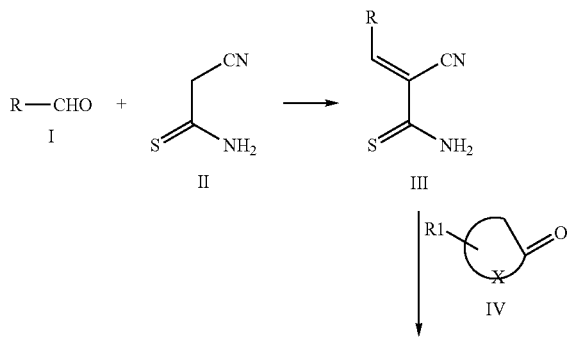

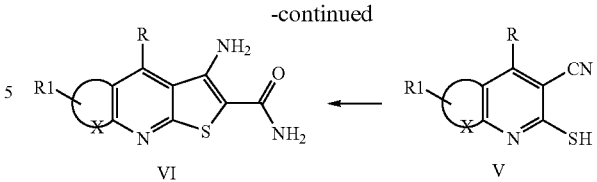

For example, as illustrated in Scheme II, beginning with substituted or unsubstituted piperidinones, pyrrolidinones, azepanones with protected groups, the procedure above affords VIa. The protecting group of VIa is removed by methods and conditions known in the art to produce VII. Substituent $R_1$ may be modified by commonly known methods to make other desired substituents (VIII) by reaction of VII with an additional reagent such as an alkyl halide, aromatic or aliphatic carboxylic acid, acid halides, sulfonyl halide, anhydride, isocyanate, and isothiocyanate, in a solvent such as DMF, dichloromethane, THF, in the presence of a suitable base such as triethylamine, diisopropylethylamine, pyridine, and potassium carbonate.

Scheme II

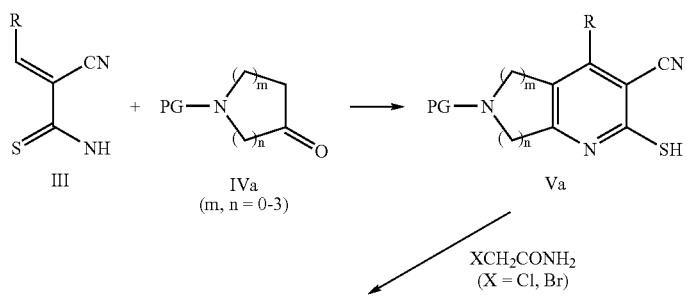

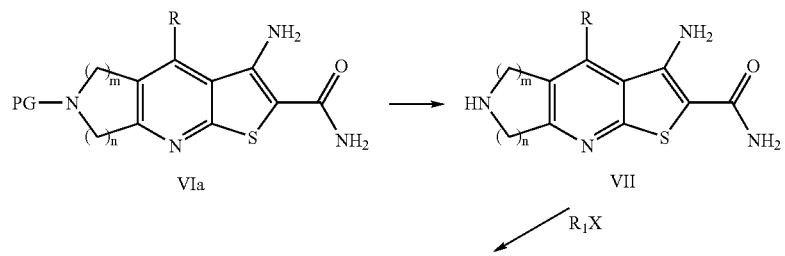

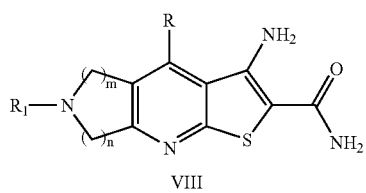

Synthetic Procedures

EXAMPLES

Example I

Synthesis of 3-amino-6-benzyl-4-thiophen-2-yl-6,7-dihydro-5H-1-thia-6,8-diaza-s-indacene-2-carboxylic acid amide (21)

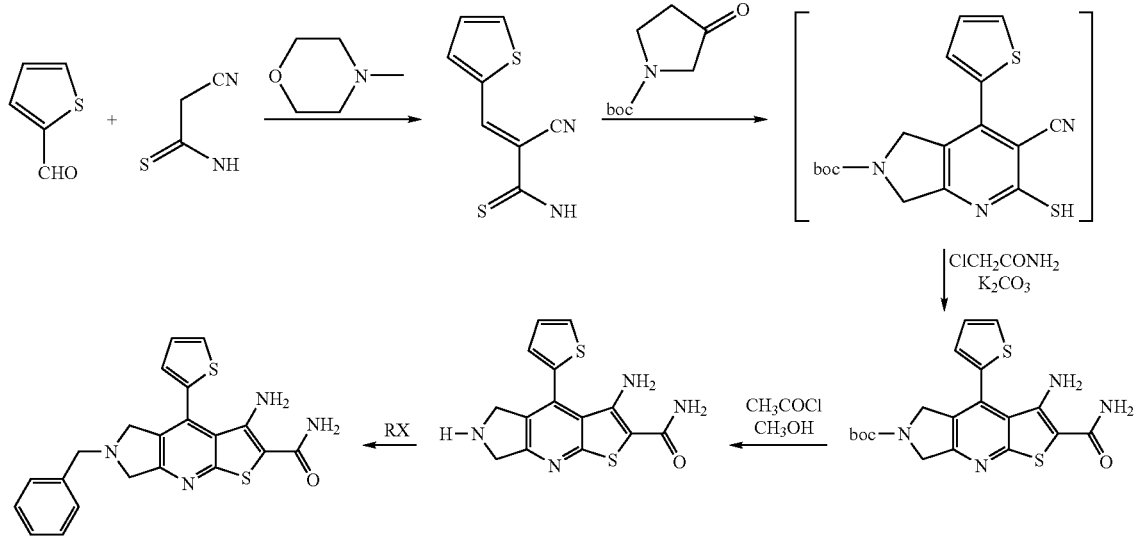

2-Cyano-3-thiophen-2-yl-thioacrylamide

To a mixture of 2-thiophencarbaldehyde (22.4 g, 0.2 mol) and 2-cyanothioacetamide (22 g, 0.22 mol) in 250 ml of ethanol was added N-methylmorpholine (30.3 g, 0.3 mol) at room temperature. The resulting mixture was stirred at room temperature overnight. The solid was filtered and washed with ethanol to give 28.2 g (72%) of product as a yellow solid after drying in vacuo. $^1$H-NMR (300 MHz, DMSO-d6): δ 10.0 (brs, 1H), 9.45 (brs, 1H), 8.37 (s, 1H), 8.12 (d, J=4.8 Hz, 1H), 7.88 (d, J=3.3 Hz, 1H), 7.32 (dd, J=3.3, 4.8 Hz, 1H). ES MS m/z 195 (M+H)$^+$, 193(M−H)$^-$.

3-Amino-2-carbamoyl-4-thiophen-2-yl-5,7-dihydro-1-thia-6,8-diaza-s-indacene-6-carboxylic acid tert-butyl ester (1)

To a mixture of 2-cyano-3-thiophen-2-yl-thioacrylamide (4.38 g, 22.5 mmol) and 1-boc-3-pyrrolidine synthesized from pyrrolidinol by reference procedures (Synthetic Commun. 1985, 15(7), 587-598) (4.16 g, 22.5 mmol) in 200 ml of anhydrous ethanol was added morpholine (3.94 g, 45 mmol) at room temperature with stirring. The resulting mixture was heated to reflux overnight. Then, 2-chloroacetamide (4.21 g, 45 mmol) and K$_2$CO$_3$ (6.23 g, 45 mmol) were added. The reaction mixture was continued to heat at 80° C. overnight and then cooled to room temperature. The crystals was filtered and washed with ethanol and water to give the desired product as yellow crystals. $^1$H-NMR (300 MHz, DMSO-d6): δ 7.92 (dd, J=1.2, 5.1 Hz, 1H), 7.33 (dd, J=1.2, 3.6 Hz, 1H), 7.30 (dd, J=3.6, 5.1 Hz, 1H), 7.26 (brs, 1H), 5.97 (d, J=10.5 Hz, 2H), 4.70 (d, J=6.0 Hz, 2H), 4.45 (d, J=10.5 Hz, 2H), 1.42 (m, 9H). ES MS m/z 417 (M+H)$^+$, 415 (M−H)$^-$.

3-Amino-4-thiophen-2-yl-6,7-dihydro-5H-1-thia-6,8-diaza-s-indacene-2-carboxylic acid amide hydrochloride (2)

To a suspension of 3-amino-2-carbamoyl-4-thiophen-2-yl-5,7-dihydro-1-thia-6,8-diaza-s-indacene-6-carboxylic acid tert-butyl ester (4 g, 9.6 mmol)) in 70 ml of anhydrous methanol was added dropwise 7 ml of acetyl chloride under argon. The resulting mixture was stirred for 48 hours at room temperature. The solid was filtered and washed with methanol to give 3.14 g (93%) of the yellow product as its hydrochloride salt. $^1$H-NMR (300 MHz, DMSO-d6): δ 10.20 (brs, 2H), 7.96 (dd, J=1.2, 5.1 Hz, 1H), 7.36 (dd, J=1.2, 3.6 Hz, 1H), 7.32 (brs, 2H), 7.31 (dd, J=3.6, 5.1 Hz, 1H), 6.02 (brs, 2H), 4.63 (s, 2H), 4.42 (s, 2H). ES MS m/z 317 (M+H)$^+$, 315 (M−H)$^-$.

3-Amino-6-benzyl-4-thiophen-2-yl-6,7-dihydro-5H-1-thia-6,8-diaza-s-indacene-2-carboxylic acid amide (21)

A mixture of 3-amino-4-thiophen-2-yl-6,7-dihydro-5H-1-thia-6,8-diaza-s-indacene-2-carboxylic acid amide hydrochloride (70 mg, 0.2 mmol), benzyl bromide (38 mg, 0.22 mmol), and triethylamine (0.2 ml) in 2 ml of anhydrous DMF was heated at 60° C. for 24 hours. The solvent was removed in vacuo, and the residue was purified by preparative HPLC to give a yellow solid. $^1$H-NMR (300 MHz, DMSO-d6): δ 7.83 (d, J=5.1 Hz, 1H), 7.32 (m, 3H), 7.31 (d, J=3.6 Hz, 1H), 7.26 (dd, J=3.6, 5.1 Hz, 1H), 7.22 (m, 2H), 7.22 (brs, 2H), 5.96 (brs, 2H), 4.02 (s, 2H), 3.86 (s, 2H), 3.72 (s, 2H). ES MS m/z 407 (M+H)$^+$, 405 (M−H)$^-$.

The following compounds were prepared by using the same procedure described in Example 1, substituting a suitable aldehyde for 2-thiophencarbaldehyde as the starting material. In some cases, if the product was not recrystallized from methanol or ethanol, the reaction mixture was purified by flash column chromatography or preparative HPLC.

3-Amino-6-pyridin-2-ylmethyl-4-thiophen-2-yl-6,7-dihydro-5H-1-thia-6,8-diaza-s-indacene-2-carboxylic acid amide (7)

3-Amino-6-pyridin-3-ylmethyl-4-thiophen-2-yl-6,7-dihydro-5H-1-thia-6,8-diaza-s-indacene-2-carboxylic acid amide (20)

3-Amino-6-(2-methyl-benzyl)-4-thiophen-2-yl-6,7-dihydro-5H-1-thia-6,8-diaza-s-indacene-2-carboxylic acid amide (22)

3-Amino-6-(3-fluoro-benzyl)-4-thiophen-2-yl-6,7-dihydro-5H-1-thia-6,8-diaza-s-indacene-2-carboxylic acid amide (23)

3-Amino-6-(3,5-dimethoxy-benzyl)-4-thiophen-2-yl-6,7-dihydro-5H-1-thia-6,8-diaza-s-indacene-2-carboxylic acid amide (24)

Example 2

Synthesis of 3-amino-6-cyclopropylmethyl-4-thiophen-2-yl-6,7-dihydro-5H-1-thia-6,8-diaza-s-indacene-2-carboxylic acid amide (8)

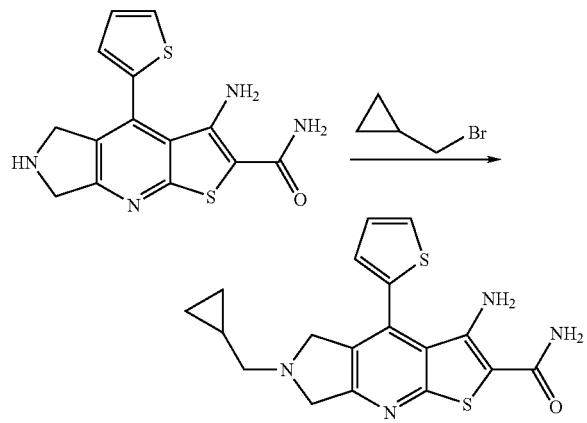

A mixture of 3-amino-4-thiophen-2-yl-6,7-dihydro-5H-1-thia-6,8-diaza-s-indacene-2-carboxylic acid amide hydrochloride (70 mg, 0.2 mmol), bromomethyl cyclopropane (54 mg, 0.4 mmol), and triethylamine (0.2 ml) in 2 ml of anhydrous DMF was heated at 60° C. for 24 hours. The solvent was removed in vacuo and the residue was purified by preparative HPLC to give pure products as a yellow solid. $^1$H-NMR (500 MHz, DMSO-d6): δ 8.00 (d, J=5.1 Hz, 1H), 7.31 (d, J=3.6 Hz, 1H), 7.26 (dd, J=3.6, 5.1 Hz, 1H), 7.22 (brs, 2H), 6.05 (brs, 2H), 4.90 (s, 2H), 4.75 (s, 2H), 3.30 (d, J=7.0 Hz, 2H), 1.15 (m, 1H), 0.65 (m, 2H), 0.40 (m, 2H). ES MS m/z 371 (M+H)$^+$, 369(M−H)$^-$.

The following compounds were prepared by using the same procedure described in Example 2, substituting a suitable halide for bromomethyl cyclopropane. In some cases, if the product was not recrystallized from methanol or ethanol, the reaction mixture was purified by flash column or preparative HPLC.

3-Amino-6-(3-chloro-propyl)-4-thiophen-2-yl-6,7-dihydro-5H-1-thia-6,8-diaza-s-indacene-2-carboxylic acid amide (3)

3-Amino-6-(tetrahydro-pyran-2-ylmethyl)-4-thiophen-2-yl-6,7-dihydro-5H-1-thia-6,8-diaza-s-indacene-2-carboxylic acid amide (4)

3-Amino-6-[5-(2-methoxy-phenyl)-[1,2,4]oxadiazol-3-ylmethyl]-4-thiophen-2-yl-6,7-dihydro-5H-1-thia-6,8-diaza-s-indacene-2-carboxylic acid amide (5)

3-Amino-6-(3-methyl-butyl)-4-thiophen-2-yl-6,7-dihydro-5H-1-thia-6,8-diaza-s-indacene-2-carboxylic acid amide (6)

3-Amino-6-(2-benzoyloxy-ethyl)-4-thiophen-2-yl-6,7-dihydro-5H-1-thia-6,8-diaza-s-indacene-2-carboxylic acid amide (9)

3-Amino-6-phenethyl-4-thiophen-2-yl-6,7-dihydro-5H-1-thia-6,8-diaza-s-indacene-2-carboxylic acid amide (10)

3-Amino-6-cyclohexylmethyl-4-thiophen-2-yl-6,7-dihydro-5H-1-thia-6,8-diaza-s-indacene-2-carboxylic acid amide (11)

3-Amino-6-[2-(4-chloro-phenyl)-2-oxo-ethyl]-4-thiophen-2-yl-6,7-dihydro-5H-1-thia-6,8-diaza-s-indacene-2-carboxylic acid amide (12)

3-Amino-6-(3-hydroxy-2-methyl-propyl)-4-thiophen-2-yl-6,7-dihydro-5H-thia-6,8-diaza-s-indacene-2-carboxylic acid amide (13)

3-Amino-6-isobutyl-4-thiophen-2-yl-6,7-dihydro-5H-1-thia-6,8-diaza-s-indacene-2-carboxylic acid amide (14)

3-Amino-6-(2-hydroxy-ethyl)-4-thiophen-2-yl-6,7-dihydro-5H-1-thia-6,8-diaza-s-indacene-2-carboxylic acid amide (15)

3-Amino-6-pentyl-4-thiophen-2-yl-6,7-dihydro-5H-1-thia-6,8-diaza-s-indacene-2-carboxylic acid amide (16)

3-Amino-6-(2-methoxy-ethyl)-4-thiophen-2-yl-6,7-dihydro-5H-1-thia-6,8-diaza-s-indacene-2-carboxylic acid amide (17)

3-Amino-6-carbethoxymethyl-4-thiophen-2-yl-6,7-dihydro-5H-1-thia-6,8-diaza-s-indacene-2-carboxylic acid amide (18)

3-Amino-6-[2-(1,3-dioxo-1,3-dihydro-isoindol-2-yl)-ethyl]-4-thiophen-2-yl-6,7-dihydro-5H-1-thia-6,8-diaza-s-indacene-2-carboxylic acid amide (19)

Example 3

Synthesis of 3-amino-6-(3-morpholin-4-yl-propyl)-4-thiophen-2-yl-6,7-dihydro-5H-1-thia-6,8-diaza-s-indacene-2-carboxylic acid amide (27)

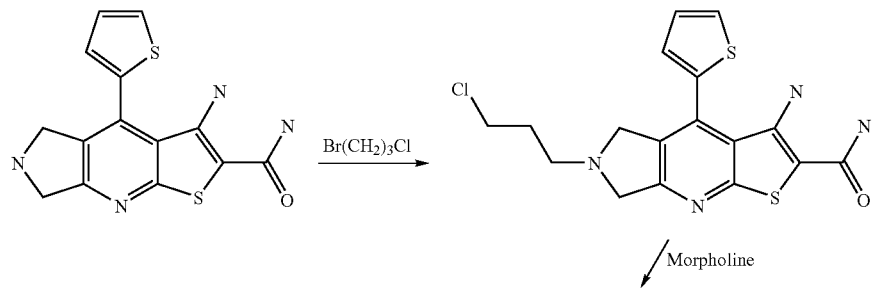

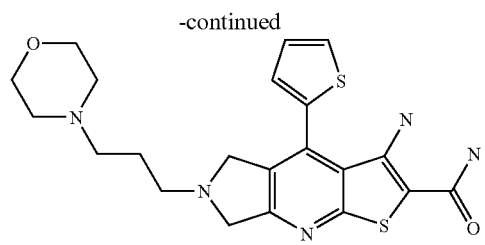

3-Amino-6-(3-chloro-propyl)-4-thiophen-2-yl-6,7-dihydro-5H-1-thia-6,8-diaza-s-indacene-2-carboxylic acid amide (3)

A mixture of 3-amino-4-thiophen-2-yl-6,7-dihydro-5H-1-thia-6,8-diaza-s-indacene-2-carboxylic acid amide hydrochloride (0.7 g, 2 mmol), 1-chloro-3-bromopropane (4 mmol), and triethylamine (2 ml) in 10 ml of anhydrous DMF was heated at 60° C. for 24 hours. The solvent was removed in vacuo, and the residue was purified by silica gel column (chloroform/methanol, 40:1) to give pure compound as a yellow solid. $^1$H-NMR (300 MHz, DMSO-d6): δ 7.88 (d, J=5.1 Hz, 1H), 7.29 (d, J=3.6 Hz, 1H), 7.27 (dd, J=3.6, 5.1 Hz, 1H), 7.22 (brs, 2H), 5.98 (brs, 2H), 4.00 (s, 2H), 3.77 (s, 2H), 3.67 (t, J=6.3 Hz, 2H), 2.78 (t, J=6.3 Hz, 2H), 1.90 (m, 2H). ES MS m/z 393, 395 (M+H)$^+$.

3-Amino-6-(3-morpholin-4-yl-propyl)-4-thiophen-2-yl-6,7-dihydro-5H-1-thia-6,8-diaza-s-indacene-2-carboxylic acid amide (27)

A mixture of 3-amino-6-(3-chloro-propyl)-4-thiophen-2-yl-6,7-dihydro-5H-1-thia-6,8-diaza-s-indacene-2-carboxylic acid amide (78 mg, 0.2 mmol) and morpholine (44 mg, 0.5 mmol) in 4 ml of ethanol was heated at 100° C. for 24 hours. The solvent was removed in vacuo, and the residue was purified by silica gel column (chloroform/methanol, 30:1) to give the pure compound as a yellow solid. $^1$H-NMR (300 MHz, DMSO-d6): δ 7.88 (d, J=5.1 Hz, 1H), 7.29 (d, J=3.6 Hz, 1H), 7.27 (dd, J=3.6, 5.1 Hz, 1H), 7.22 (brs, 2H), 5.98 (brs, 2H), 4.59 (s, 2H), 4.35 (s, 2H), 3.80 (m, 4H), 3.67 (t, J=6.3 Hz, 2H), 3.20 (m, 4H), 3.15 (t, J=6.3 Hz, 2H), 2.00 (m, 2H). ES MS m/z 444 (M+H)$^+$, 442 (M−H)$^-$.

The following compounds were prepared by the same procedure described in Example 3, substituting suitable nucleophilic reagents for morpholine, as for compound 27. In some cases, if the product was not recrystallized from methanol or ethanol, the reaction mixture was purified by flash column chromatography or preparative HPLC.

3-Amino-6-[3-(4-pyrimidin-2-yl-piperazin-1-yl)-propyl]-4-thiophen-2-yl-6,7-dihydro-5H-1-thia-6,8-diaza-s-indacene-2-carboxylic acid amide (25)

3-Amino-6-[3-(2-methoxy-piperidin-1-yl)-propyl]-4-thiophen-2-yl-6,7-dihydro-5H-1-thia-6,8-diaza-s-indacene-2-carboxylic acid amide (26)

3-Amino-6-[3-(2-hydroxy-propylamino)-propyl]-4-thiophen-2-yl-6,7-dihydro-5H-1-thia-6,8-diaza-s-indacene-2-carboxylic acid amide (28)

Example 4

Synthesis of 3-amino-7-benzyl-4-thiophen-2-yl-5,6,7,8-tetrahydro-1-thia-7,9-diaza-cyclopenta[b]naphthalene-2-carboxylic acid amide (31)

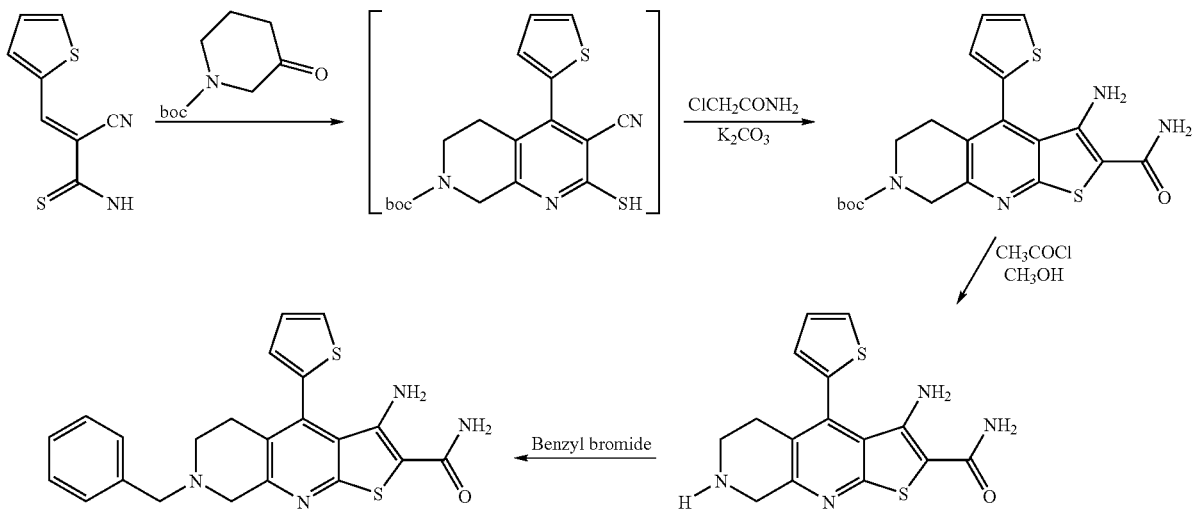

3-Amino-2-carbamoyl-4-thiophen-2-yl-5,8-dihydro-6H-1-thia-7,9-diaza-cyclopenta[b]naphthalene-7-carboxylic acid tert-butyl ester (30)

To a mixture of 2-cyano-3-thiophen-2-yl-thioacrylamide (4.38 g, 22.5 mmol) and 1-boc-3-piperidone (4.49 g, 22.5 mmol) in 200 ml of anhydrous ethanol was added morpholine (3.94 g, 45 mmol) at room temperature with stirring. The resulting mixture was heated to reflux overnight. Then, 2-chloroacetamide (4.21 g, 45 mmol) and K₂CO₃ (6.23 g, 45 mmol) was added. The reaction mixture was continued to heat at 80° C. overnight. The solvent was removed in vacuo, and the residue was purified by silica gel column (chloroform/methanol, 40:1) and recrystallized from methanol to give a yellow crystalline product.

3-Amino-4-thiophen-2-yl-5,6,7,8-tetrahydro-1-thia-7,9-diaza-cyclopenta[b]naphthalene-2-carboxylic acid amide (29)

To a suspension of 3-amino-2-carbamoyl-4-thiophen-2-yl-5,8-dihydro-6H-1-thia-7,9-diaza-cyclopenta[b]naphthalene-7-carboxylic acid tert-butyl ester (100 mg) in 10 ml of anhydrous methanol under argon 0.5 ml of acetyl chloride was added dropwise, and the resulting mixture was stirred overnight at room temperature. The reaction mixture was neutralized with 7N ammonia in methanol and evaporated to dryness under vacuum. The residue was purified by silica gel column (chloroform/methanol, 30:1) to give a yellow solid. ¹H-NMR (300 MHz, DMSO-d6): δ 7.88 (d, J=5.1 Hz, 1H), 7.28 (dd, J=3.6, 5.1 Hz, 1H), 7.16 (d, J=3.6 Hz, 1H), 7.01 (brs, 2H), 5.64 (brs, 2H), 4.84 (brs, 1H), 3.16 (s, 2H), 2.94 (m, 2H), 1.86 (m, 2H). ES MS m/z 331 (M+H)⁺, 329 (M−H)⁻.

3-Amino-7-benzyl-4-thiophen-2-yl-5,6,7,8-tetrahydro-1-thia-7,9-diaza-cyclopenta[b]naphthalene-2-carboxylic acid amide (31)

A mixture of 3-amino-4-thiophen-2-yl-5,6,7,8-tetrahydro-1-thia-7,9-diaza-cyclopenta[b]naphthalene-2-carboxylic acid amide (66 mg, 0.2 mmol), benzyl bromide (38 mg, 0.22 mmol), and triethylamine (0.2 ml) in 2 ml of anhydrous DMF was heated at 60° C. for 24 hours. The solvent was removed in vacuo, and the residue was purified by preparative HPLC to give pure products as a yellow solid.

The following compounds were prepared by using the same procedure described in Example 4 and substituting a suitable halide for benzyl bromide as for compound 31. In some cases, if the product was not recrystallized from methanol or ethanol, the reaction mixture was purified by flash column or preparative HPLC.

3-Amino-6-tert-butyloxycarbonyl-4-thiophen-2-yl-5,6,7,8-tetrahydro-thieno[2,3-b][1,6]naphthyridine-2-carboxylic acid amide (32)

3-Amino-6-benzyl-4-(5-methyl-furan-2-yl)-5,6,7,8-tetrahydro-thieno[2,3-b][1,6]naphthyridine-2-carboxylic acid amide (33)

Example 5

Synthesis of 3-amino-7-ethoxy-4-thiophen-2-yl-6,7-dihydro-5H-cyclopenta[b]thieno[3,2-e]pyridine-2-carboxylic acid amide (35)

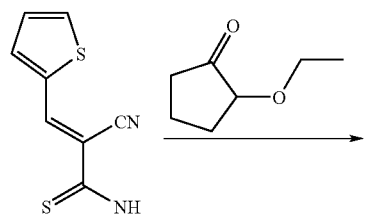

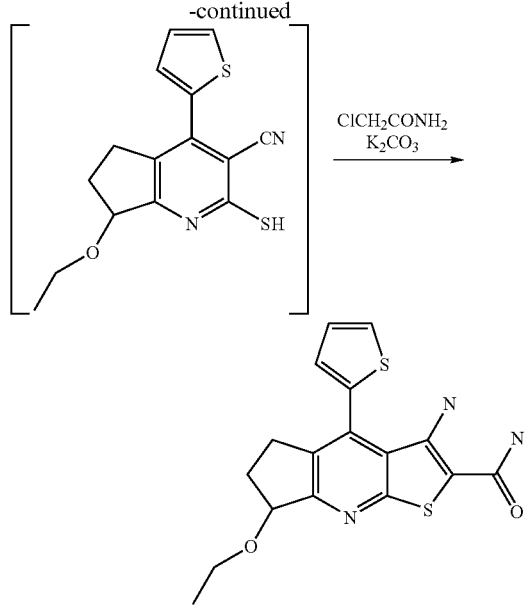

3-Amino-7-ethoxy-4-thiophen-2-yl-6,7-dihydro-5H-cyclopenta[b]thieno[3,2-e]pyridine-2-carboxylic acid amide (35)

To a mixture of 2-cyano-3-thiophen-2-yl-thioacrylamide (0.39 g, 2 mmol), 2-ethoxy-cyclopentanone (0.26 g, 2 mmol) in 10 ml of ethanol was added N-methylmorpholine (0.4 g, 4 mmol). The resulting mixture was refluxed overnight, and 2-chloroacetamide (0.38 g, 4 mmol) and anhydrous potassium carbonate (0.55 g, 4 mmol) were added with stirring. The reaction mixture was further heated at reflux overnight. The cooled reaction mixture was poured into 50 ml of ice-water, and the precipitate was filtered and washed with water to give the crude product as a yellow solid. The product was further purified by silica gel column to produce a yellow solid. ¹H-NMR (300 MHz, DMSO-d6): δ 7.88 (dd, J=2.7, 3.6 Hz, 1H), 7.28-7.26 (m, 2H), 7.24 (brs, 2H), 5.8 (brs, 2H), 4.87 (dd, J=4.5, 6.9 Hz, 1H), 3.79 (m, 1H), 3.65 (m, 1H), 3.43 (m, 1H), 2.77 (m, 1H), 2.35 (m, 1H), 1.98 (m, 1H), 1.31 (t, J=6.9 Hz, 3H). ES MS m/z 360 (M+H)⁺, 358 (M−H)⁻.

The following compounds were prepared by the same procedure described in Example 5, substituting a suitable cyclic ketone for 2-ethoxy-cyclopentanone as for compound 35. When flash column chromatography was insufficient for purification, the crude product was further purified by preparative HPLC.

3-Amino-7-methyl-4-thiophen-2-yl-6,7-dihydro-5H-cyclopenta[b]thieno[3,2-e]pyridine-2-carboxylic acid amide (37)

3-Amino-7-carbomethoxymethyl-4-thiophen-2-yl-6,7-dihydro-5H-cyclopenta[b]thieno[3,2-e]pyridine-2-carboxylic acid amide (40)

3-Amino-7-carbethoxymethyl-4-thiophen-2-yl-6,7-dihydro-5H-cyclopenta[b]thieno[3,2-e]pyridine-2-carboxylic acid amide (41)

3-Amino-7-hexyl-4-thiophen-2-yl-6,7-dihydro-5H-cyclopenta[b]thieno[3,2-e]pyridine-2-carboxylic acid amide (59)

3-Amino-7-heptyl-4-thiophen-2-yl-6,7-dihydro-5H-cyclopenta[b]thieno[3,2-e]pyridine-2-carboxylic acid amide (60)

3-Amino-7-cyclopentyl-4-thiophen-2-yl-6,7-dihydro-5H-cyclopenta[b]thieno[3,2-e]pyridine-2-carboxylic acid amide (61)

3-Amino-8-(2-cyano-ethyl)-4-thiophen-2-yl-5,6,7,8-tetrahydro-thieno[2,3-b]quinoline-2-carboxylic acid amide (62)

3-Amino-8-isobutyl-4-thiophen-2-yl-5,6,7,8-tetrahydro-thieno[2,3-b]quinoline-2-carboxylic acid amide (63)

3-Amino-8-benzyl-4-thiophen-2-yl-5,6,7,8-tetrahydro-thieno[2,3-b]quinoline-2-carboxylic acid amide (64)

3-Amino-8-propyl-4-thiophen-2-yl-5,6,7,8-tetrahydro-thieno[2,3-b]quinoline-2-carboxylic acid amide (65)

3-Amino-8-phenyl-4-thiophen-2-yl-5,6,7,8-tetrahydro-thieno[2,3-b]quinoline-2-carboxylic acid amide (66)

3-Amino-8-(3-methoxy-phenyl)-4-thiophen-2-yl-5,6,7,8-tetrahydro-thieno[2,3-b]quinoline-2-carboxylic acid amide (67)

3-Amino-8-cyclohexyl-4-thiophen-2-yl-5,6,7,8-tetrahydro-thieno[2,3-b]quinoline-2-carboxylic acid amide (68)

3-Amino-8-methoxy-4-thiophen-2-yl-5,6,7,8-tetrahydro-thieno[2,3-b]quinoline-2-carboxylic acid amide (69)

8-Allyl-3-amino-4-thiophen-2-yl-5,6,7,8-tetrahydro-thieno[2,3-b]quinoline-2-carboxylic acid amide (70)

3-Amino-8-carbethoxymethyl-4-thiophen-2-yl-5,6,7,8-tetrahydro-thieno[2,3-b]quinoline-2-carboxylic acid amide (71)

3-Amino-6-methyl-4-thiophen-2-yl-5,6,7,8-tetrahydro-thieno[2,3-b]quinoline-2-carboxylic acid amide (72)

3-Amino-6-ethyl-4-thiophen-2-yl-5,6,7,8-tetrahydro-thieno[2,3-b]quinoline-2-carboxylic acid amide (73)

3-Amino-7-methyl-4-thiophen-2-yl-5,6,7,8-tetrahydro-thieno[2,3-b]quinoline-2-carboxylic acid amide (74)

3-Amino-4-(3-methyl-thiophen-2-yl)-5-oxo-5,6,7,8-tetrahydro-thieno[2,3-b]quinoline-2-carboxylic acid amide (75)

3-Amino-4-(thiophen-2-yl)-5-oxo-5,6,7,8-tetrahydro-thieno[2,3-b]quinoline-2-carboxylic acid amide (76)

3-Amino-4-(4-chloro-phenyl)-5-oxo-5,6,7,8-tetrahydro-thieno[2,3-b]quinoline-2-carboxylic acid amide (77)

3-Amino-5-oxo-4-thiophen-2-yl-1,4,5,6,7,8-hexahydro-thiochromeno[2,3-b]pyrrole-2-carboxylic acid amide (78)
A by-product from synthesis of 3-amino-4-(thiophen-2-yl)-5-oxo-5,6,7,8-tetrahydro-thieno[2,3-b]quinoline-2-carboxylic acid amide (76)

Example 6

Synthesis of 3-amino-7-(2-morpholin-4-yl-2-oxo-ethyl)-4-thiophen-2-yl-6,7-dihydro-5H-cyclopenta[b]thieno[3,2-e]pyridine-2-carboxylic acid amide (38)

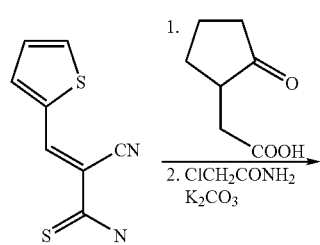

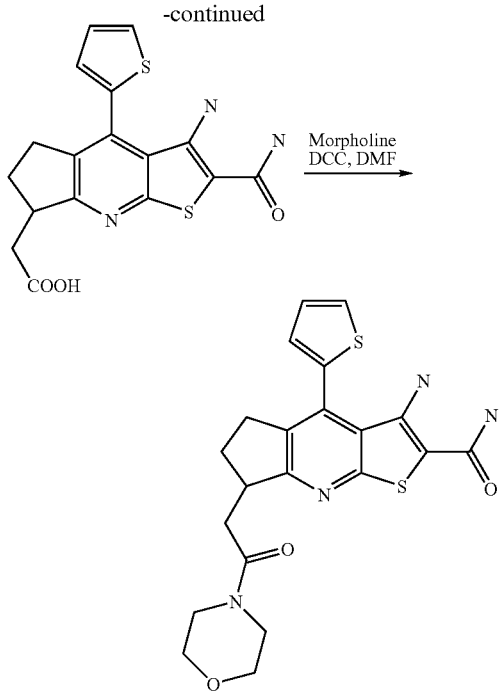

3-Amino-7-carboxymethyl-4-thiophen-2-yl-6,7-dihydro-5H-cyclopenta[b]thieno [3,2-e]pyridine-2-carboxylic acid amide (36)

To a mixture of 2-cyano-3-thiophen-2-yl-thioacrylamide (6.3 g, 33 mmol), 2-oxocyclopentaneacetic acid (4.6 g, 33 mmol) in 70 ml of ethanol was added N-methylmorpholine (6.6 g, 65 mmol). The resulting mixture was refluxed overnight, then 2-chloroacetamide (6.1 g, 65 mmol) and anhydrous potassium carbonate (9.0 g, 65 mmol) was added with stirring. The reaction mixture was continued to reflux overnight. The reaction mixture was cooled to room temperature and the solid was filtered and washed with ethanol. The sodium salt of product was dissolved in 100 ml of water and neutralized with 10% hydrochloric acid to pH<6. The precipitate was filtered and washed with water to give 3.7 g (31%) of pure product as a yellow solid. $^1$H-NMR (300 MHz, DMSO-d6): δ 12.24 (brs, 1H), 7.87 (d, J=5.1 Hz, 1H), 7.27-7.24 (m, 2H), 7.18 (brs, 2H), 5.93 (brs, 2H), 3.55 (m, 1H), 2.94 (dd, J=3.9, 16.2 Hz, 1H), 2.68 (m, 2H), 2.40 (m, 2H), 1.75 (m, 1H). ES MS m/z 374 (M+H)$^+$, 372 (M−H)$^−$.

3-Amino-7-(2-morpholin-4-yl-2-oxo-ethyl)-4-thiophen-2-yl-6,7-dihydro-5H-cyclopenta[b]thieno[3,2-e]pyridine-2-carboxylic acid amide (38)

A solution of 3-amino-7-carboxymethyl-4-thiophen-2-yl-6,7-dihydro-5H-cyclopenta[b]thieno[3,2-e]pyridine-2-carboxylic acid amide (75 mg, 0.2 mmol), morpholine (19 mg, 0.22 mmol), and 1-hydroxybenzotriazole (30 mg, 0.22 mmol) in 2 ml of anhydrous DMF was cooled to 0° C., then DCC (45 mg, 0.22 mmol) was added. The resulting mixture was stirred at 0° C. for 2 hours, then at room temperature for 48 hours. The solvent was removed in vacuo and the residue was recrystallized from methanol to give a pure product as yellow crystals. $^1$H-NMR (300 MHz, DMSO-d6): δ 7.87 (dd, J=1.2, 4.8 Hz, 1H), 7.27 (dd, J=3.6, 4.8 Hz, 1H), 7.23 (dd, J=1.2, 3.6 Hz, 1H), 7.18 (brs, 2H), 5.93 (brs, 2H), 3.61 (m, 1H), 3.55 (m, 4H), 3.47 (m, 4H), 3.04 (dd, J=3.9, 15.9 Hz, 1H), 2.71 (m, 2H), 2.57 (dd, J=9.3, 15.9 Hz, 1H), 2.39 (m, 1H), 1.75 (m, 1H). ES MS m/z 443 (M+H)$^+$, 441 (M−H)$^−$.

The following compounds were prepared by the same procedure described in Example 6, substituting a suitable amine for morpholine as for compound 38. In some cases, if the product was not recrystallized from methanol or ethanol, the reaction mixture was purified by flash column or preparative HPLC.

3-Amino-7-[(2-hydroxy-2-phenyl-ethylcarbamoyl)-methyl]-4-thiophen-2-yl-6,7-dihydro-5H-cyclopenta[b]thieno[3,2-e]pyridine-2-carboxylic acid amide (39)

3-Amino-7-methylcarbamoylmethyl-4-thiophen-2-yl-6,7-dihydro-5H-cyclopenta[b]thieno[3,2-e]pyridine-2-carboxylic acid amide (42)

3-Amino-7-{[(5-methyl-furan-2-ylmethyl)-carbamoyl]-methyl}-4-thiophen-2-yl-6,7-dihydro-5H-cyclopenta[b]thieno[3,2-e]pyridine-2-carboxylic acid amide (43)

3-Amino-7-[(2-methoxy-benzylcarbamoyl)-methyl]-4-thiophen-2-yl-6,7-dihydro-5H-cyclopenta[b]thieno[3,2-e]pyridine-2-carboxylic acid amide (44)

3-Amino-7-{[(pyridin-2-ylmethyl)-carbamoyl]-methyl}-4-thiophen-2-yl-6,7-dihydro-5cyclopenta[b]thieno[3,2-e]pyridine-2-carboxylic acid amide (45)

3-Amino-7-[(2-pyridin-2-yl-ethylcarbamoyl)-methyl]-4-thiophen-2-yl-6,7-dihydro-5H-cyclopenta[b]thieno[3,2-e]pyridine-2-carboxylic acid amide (46)

3-Amino-4-thiophen-2-yl-7-[(4-trifluoromethyl-benzylcarbamoyl)-methyl]-6,7-dihydro-5H-cyclopenta[b]thieno[3,2-e]pyridine-2-carboxylic acid amide (47)

3-Amino-7-[(3-methyl-butylcarbamoyl)-methyl]-4-thiophen-2-yl-6,7-dihydro-5H-cyclopenta[b]thieno[3,2-e]pyridine-2-carboxylic acid amide (48)

3-Amino-7-dimethylcarbamoylmethyl-4-thiophen-2-yl-6,7-dihydro-5H-cyclopenta[b]thieno[3,2-e]pyridine-2-carboxylic acid amide (49)

3-Amino-7-cyclobutylcarbamoylmethyl-4-thiophen-2-yl-6,7-dihydro-5H-cyclopenta[b]thieno[3,2-e]pyridine-2-carboxylic acid amide (50)

3-Amino-7-cyclohexylcarbamoylmethyl-4-thiophen-2-yl-6,7-dihydro-5H-cyclopenta[b]thieno[3,2-e]pyridine-2-carboxylic acid amide (51)

3-Amino-7-[2-(4-hydroxy-piperidin-1-yl)-2-oxo-ethyl]-4-thiophen-2-yl-6,7-dihydro-5H-cyclopenta[b]thieno[3,2-e]pyridine-2-carboxylic acid amide (52)

3-Amino-7-[2-oxo-2-(4-pyridin-2-yl-piperazin-1-yl)-ethyl]-4-thiophen-2-yl-6,7-dihydro-5H-cyclopenta[b]thieno[3,2-e]pyridine-2-carboxylic acid amide (53)

4-[2-(3-Amino-2-carbamoyl-4-thiophen-2-yl-6,7-dihydro-5H-cyclopenta[b]thieno[3,2-e]pyridin-7-yl)-acetylamino]-piperidine-1-carboxylic acid ethyl ester (54)

3-Amino-7-{[2-(1-methyl-pyrrolidin-2-yl)-ethylcarbamoyl]-methyl}-4-thiophen-2-yl-6,7-dihydro-5H-cyclopenta[b]thieno[3,2-e]pyridine-2-carboxylic acid amide (55)

1-[2-(3-Amino-2-carbamoyl-4-thiophen-2-yl-6,7-dihydro-5H-cyclopenta[b]thieno[3,2-e]pyridin-7-yl)-acetyl]-piperidine-4-carboxylic acid ethyl ester (56)

3-Amino-7-[(3-morpholin-4-yl-propylcarbamoyl)-methyl]-4-thiophen-2-yl-6,7-dihydro-5H-cyclopenta[b]thieno[3,2-e]pyridine-2-carboxylic acid amide (57)

3-Amino-7-{[3-(2-methyl-piperidin-1-yl)-propylcarbamoyl]-methyl}-4-thiophen-2-yl-6,7-dihydro-5H-cyclopenta[b]thieno[3,2-e]pyridine-2-carboxylic acid amide (58)

Example 7

Synthesis of 3-amino-6-phenylthiocarbamoyl-4-thiophen-2-yl-6,7-dihydro-5H-1-thia-6,8-diaza-s-indacene-2-carboxylic acid amide (79)

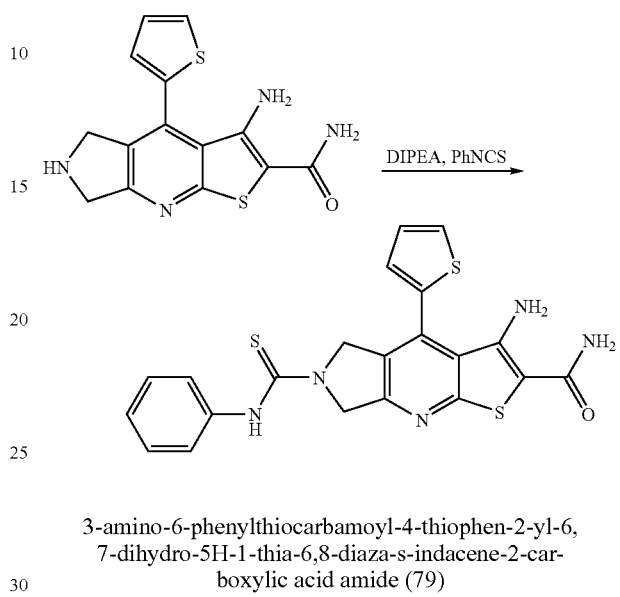

3-amino-6-phenylthiocarbamoyl-4-thiophen-2-yl-6,7-dihydro-5H-1-thia-6,8-diaza-s-indacene-2-carboxylic acid amide (79)

To 70 mg (0.22 mmol) of 3-amino-4-thiophen-2-yl-6,7-dihydro-5H-1-thia-6,8-diaza-s-indacene-2-carboxylic acid amide hydrochloride in 3.0 ml of DMF was added dropwise 40 µl of diisopropylethylamine and 26 µl of phenyl isothiocyanate with stirring at 0° C. The resulting mixture was continuously stirred at room temperature for 6 hours. The solvent was removed in vacuo and the residue was recrystallized from methanol to give the pure product as a yellow solid in 92% yield: silica gel TLC (1:5 methanol-chloroform); $^1$H NMR (300 MHz, DMSO-d6) δ 9.29 (s, 1H), 7.94 (d, 1H, J=4.8 Hz), 7.36-7.28 (m, 8H), 7.16-7.13 (m, 1H), 5.99 (s, 2H), 5.13 (s, 2H), 4.89 (s, 2H). ES MS m/z 452 (M+H)$^+$, 450 (M−H)$^−$.

The following compounds were prepared by using the same procedure described in Example 7, substituting a suitable isothiocyanate for phenyl isothiocyanate, as for compound 79. In most cases, 1.0 equivalent of 3-amino-4-thiophen-2-yl-6,7-dihydro-5H-1-thia-6,8-diaza-s-indacene-2-carboxylic acid amide hydrochloride in DMF was added dropwise 1.1 equivalent of diisopropylethylamine and 1.0 equivalent of isothiocyanate at 0° C. Then the resulting mixture was stirred at room temperature for 4 to 16 hours and monitored by TLC. The solvent was removed in vacuo and the residue was purified by a silica gel column chromatography eluting with 10-25% methanol in chloroform or recrystallized from methanol to give the pure products as a yellow solid in 80-99% yield.

3-Amino-6-[(tetrahydro-furan-2-ylmethyl)-thiocarbamoyl]-4-thiophen-2-yl-6,7-dihydro-5H-1-thia-6,8-diaza-s-indacene-2-carboxylic acid amide (80)

3-Amino-6-cyclopentylthiocarbamoyl-4-thiophen-2-yl-6,7-dihydro-5H-1-thia-6,8-diaza-s-indacene-2-carboxylic acid amide (81)

3-Amino-6-butylthiocarbamoyl-4-thiophen-2-yl-6,7-dihydro-5H-1-thia-6,8-diaza-s-indacene-2-carboxylic acid amide (82)

3-Amino-4-thiophen-2-yl-6-p-tolylthiocarbamoyl-6,7-dihydro-5H-1-thia-6,8-diaza-s-indacene-2-carboxylic acid amide (83)

3-Amino-6-benzylthiocarbamoyl-4-thiophen-2-yl-6,7-dihydro-5H-1-thia-6,8-diaza-s-indacene-2-carboxylic acid amide (84)

3-Amino-6-(3-methoxy-phenylthiocarbamoyl)-4-thiophen-2-yl-6,7-dihydro-5H-1-thia-6,8-diaza-s-indacene-2-carboxylic acid amide (85)

3-Amino-6-(3-phenyl-propylthiocarbamoyl)-4-thiophen-2-yl-6,7-dihydro-5H-1-thia-6,8-diaza-s-indacene-2-carboxylic acid amide (86)

3-Amino-4-thiophen-2-yl-6-(3-trifluoromethyl-phenylthiocarbamoyl)-6,7-dihydro-5H-1-thia-6,8-diaza-s-indacene-2-carboxylic acid amide (87)

3-Amino-6-(4-fluoro-phenylthiocarbamoyl)-4-thiophen-2-yl-6,7-dihydro-5H-1-thia-6,8-diaza-s-indacene-2-carboxylic acid amide (88)

3-Amino-6-(3,5-dichloro-phenylthiocarbamoyl)-4-thiophen-2-yl-6,7-dihydro-5H-1-thia-6,8-diaza-s-indacene-2-carboxylic acid amide (89)

4-[(3-Amino-2-carbamoyl-4-thiophen-2-yl-5,7-dihydro-1-thia-6,8-diaza-s-indacene-6-carbothioyl)-amino]-benzoic acid methyl ester (90)

3-Amino-6-cyclopropylthiocarbamoyl-4-thiophen-2-yl-6,7-dihydro-5H-1-thia-6,8-diaza-s-indacene-2-carboxylic acid amide (91)

3-Amino-6-(3,5-dimethyl-phenylthiocarbamoyl)-4-thiophen-2-yl-6,7-dihydro-5H-1-thia-6,8-diaza-s-indacene-2-carboxylic acid amide (92)

3-Amino-6-(2-morpholin-4-yl-ethylthiocarbamoyl)-4-thiophen-2-yl-6,7-dihydro-5H-1-thia-6,8-diaza-s-indacene-2-carboxylic acid amide (93)

3-Amino-6-(3-morpholin-4-yl-propylthiocarbamoyl)-4-thiophen-2-yl-6,7-dihydro-5H-1-thia-6,8-diaza-s-indacene-2-carboxylic acid amide (94)

Example 8

3-amino-6-(4,5-dihydro-thiazol-2-yl)-4-thiophen-2-yl-6,7-dihydro-5H-1-thia-6,8-diaza-s-indacene-2-carboxylic acid amide (95)

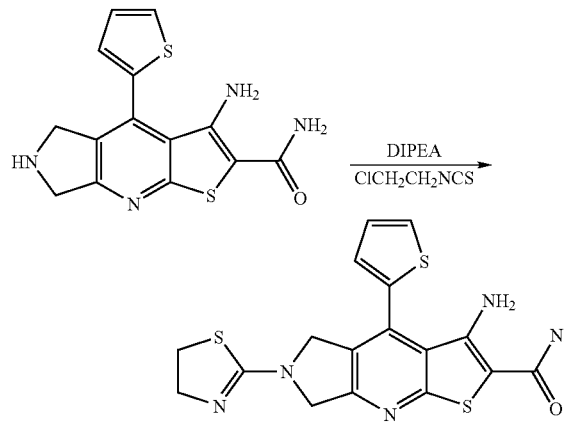

3-amino-6-(4,5-dihydro-thiazol-2-yl)-4-thiophen-2-yl-6,7-dihydro-5H-1-thia-6,8-diaza-s-indacene-2-carboxylic acid amide (162)

To 20 mg (0.06 mmol) of 3-amino-4-thiophen-2-yl-6,7-dihydro-5H-1-thia-6,8-diaza-s-indacene-2-carboxylic acid amide hydrochloride in 3.0 ml of DMF was added 51 ul of 1.0 M solution of diisopropylethylamine in THF and 7.3 mg (0.06 mmol) of 2-chloroethyl isothiocyanate at 0° C. with stirring. The resulting mixture was continuously stirred at room temperature for 16 hours. The solvent was removed in vacuo to dryness. The residue was recrystallized from methanol to give the pure product as a yellow solid in 70% yield: silica gel TLC $R_f$ 0.80 (1:8 methanol-chloroform); $^1$H NMR (300 MHz, DMSO-$d_6$) δ 7.97 (dd, 1H, J=6.0, 1.2 Hz), 7.37-7.30 (m, 4H), 6.00 (s, 2H), 5.07 (s, 2H), 4.82 (s, 2H), 3.98 (t, 2H, J=15.0 Hz), 3.68 (t, 2H, J=15.0 Hz). ES MS m/z 540 (M+H)$^+$, 538 (M−H)$^−$.

Example 9

3-amino-6-(4-cyanophenylcarbamoyl-4-thiophen-2-yl-6,7-dihydro-5H-1-thia-6,8-diaza-s-indacene-2-carboxylic acid amide (106)

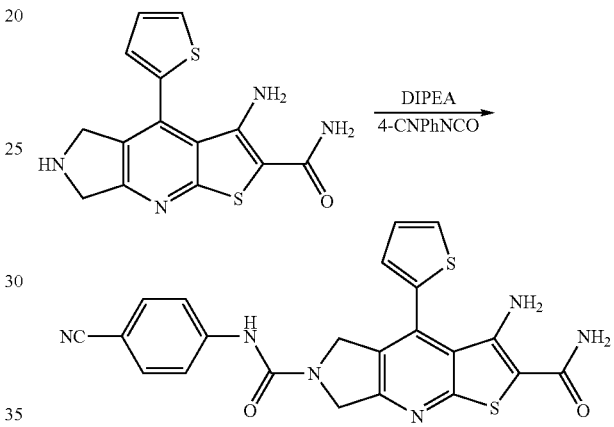

3-amino-6-(4-cyanophenylcarbamoyl-4-thiophen-2-yl-6,7-dihydro-5H-1-thia-6,8-diaza-s-indacene-2-carboxylic acid amide (106)

To 50 mg (0.158 mmol) of 3-amino-4-thiophen-2-yl-6,7-dihydro-5H-1-thia-6,8-diaza-s-indacene-2-carboxylic acid amide hydrochloride in 3.0 ml of DMF was added dropwise 0.16 ml of 1.0 M solution of diisopropylethylamine in THF and 0.16 ml of 1.0 M solution of 4-cyanophenyl isocyanate in THF with stirring at 0° C. The resulting mixture was continuously stirred at room temperature for 8 hours. The solvent was removed in vacuo to dryness. The residue was recrystallized from methanol and further purified by HPLC to give the pure product as a yellow solid in 93.7% yield: silica gel TLC $R_f$ 0.80 (1:5 methanol-chloroform); $^1$H NMR (DMSO-$d_6$) δ 8.94 (s, 1H), 7.94 (d, 1H, J=3.0 Hz), 7.73-7.67 (m, 4H), 7.36-7.27 (m, 4H), 5.98 (s, 2H), 4.92 (s, 2H), 4.68 (s, 2H). ES MS m/z 461 (M+H)$^+$, 459 (M−H)$^−$.

The following compounds were prepared by using the same procedure described in Example 9 and substituting a isocyanate for 4-cyanophenylcyanate as for compound 106. In some cases, if the product was not recrystallized from methanol or ethanol, the reaction mixture was purified by flash column chromatography or preparative HPLC.

3-Amino-4-thiophen-2-yl-5,7-dihydro-1-thia-6,8-diaza-s-indacene-2,6-dicarboxylic acid 2-amide 6-phenylamide (96)

3-Amino-4-thiophen-2-yl-5,7-dihydro-1-thia-6,8-diaza-s-indacene-2,6-dicarboxylic acid 2-amide 6-benzylamide (97)

3-Amino-4-thiophen-2-yl-5,7-dihydro-1-thia-6,8-diaza-s-indacene-2,6-dicarboxylic acid 2-amide 6-ethylamide (98)

3-Amino-4-thiophen-2-yl-5,7-dihydro-1-thia-6,8-diaza-s-indacene-2,6-dicarboxylic acid 2-amide 6-[(4-phenyl-piperazin-1-ylmethyl)-amide] (99)

3-Amino-4-thiophen-2-yl-5,7-dihydro-1-thia-6,8-diaza-s-indacene-2,6-dicarboxylic acid 2-amide 6-thiophen-3-ylamide (100)

3-Amino-4-thiophen-2-yl-5,7-dihydro-1-thia-6,8-diaza-s-indacene-2,6-dicarboxylic acid 2-amide 6-cyclohexylamide (101)

3-Amino-4-thiophen-2-yl-5,7-dihydro-1-thia-6,8-diaza-s-indacene-2,6-dicarboxylic acid 2-amide 6-[(6-morpholin-4-yl-pyridin-3-yl)-amide] (102)

Example 10

3-amino-6-(2-chloro-acetyl)-4-thiophen-2-yl-6,7-dihydro-5H-1-thia-6,8-diaza-s-indacene-2-carboxylic acid amide (104)

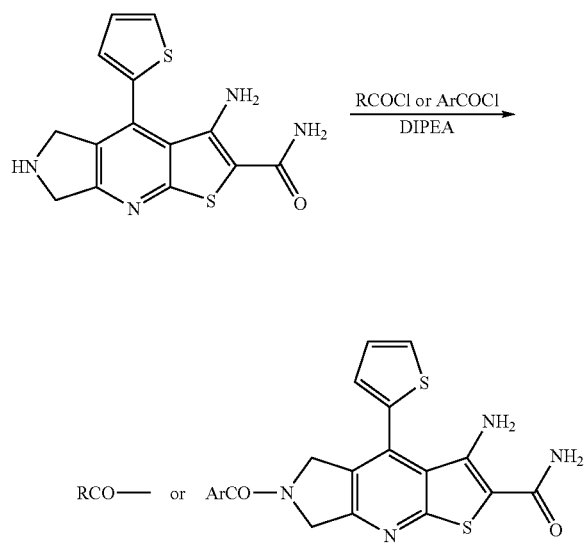

To 50 mg (0.158 mmol) of 3-amino-4-thiophen-2-yl-6,7-dihydro-5H-1-thia-6,8-diaza-s-indacene-2-carboxylic acid amide hydrochloride in 3.0 ml of DMF was added dropwise 0.32 ml of 1.0 M solution containing diisopropylethylamine (DIPEA) in THF and (0.16 mmol) of 2-chloroacetyl chloride in 1.0 ml of DMF, according to standard procedures. The resulting mixture was continuously stirred at room temperature for several hours, and the progress of the reaction was monitored by TLC. The solvent was removed under vacuum, and the residue was recrystallized from a polar solvent. Similar procedures were used for 3-amino-6-[2-(4-benzyl-cyclohexylamino)-acetyl]-4-thiophen-2-yl-6,7-dihydro-5H-1-thia-6,8-diaza-s-indacene-2-carboxylic acid amide (103) and 3-amino-6-(6-morpholin-4-yl-pyridine-3-carbonyl)-4-thiophen-2-yl-6,7-dihydro-5H-1-thia-6,8-diaza-s-indacene-2-carboxylic acid amide (105). In some cases, if the product was not recrystallized from methanol or ethanol, the reaction mixture was purified by flash column chromatography or preparative HPLC. All products were verified by NMR spectroscopy.

Example 11

8-Amino-7-thiophen-2-yl-1,2,3,4,4a,5,6,11b-octahydro-10-thia-11-aza-cyclopenta[b]phenanthrene-9-carboxylic acid amide (107)

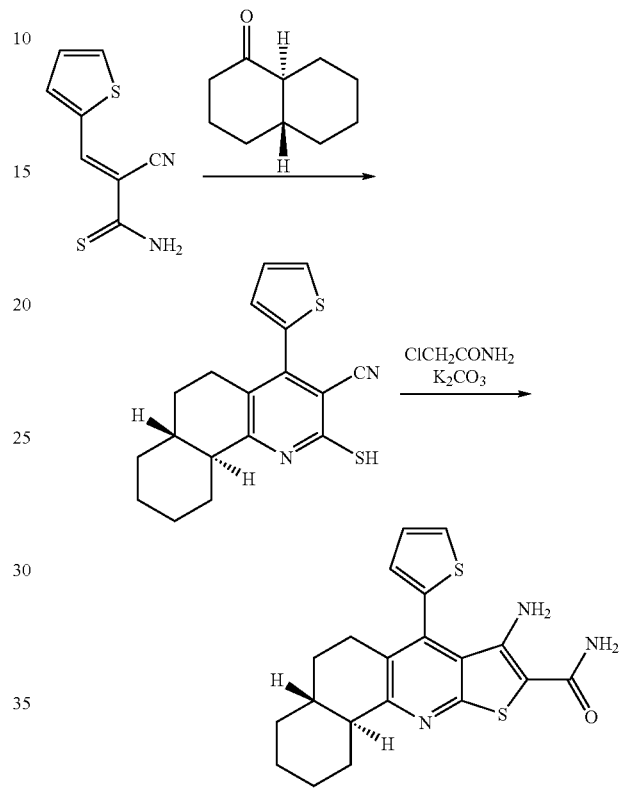

4-Thiophen-2-yl-2-thioxo-1,2,5,6,6a,7,8,9,10,10a-decahydro-benzo[h]quinoline-3-carbonitrile A mixture of 2-cyano-3-thiophen-2-yl-thioacrylamide (290 mg, 1.533 mmol), trans-1-decalone (280 mg) and morpholine (2 drops) was microwaved in a sealed vessel with the following condition: 300 watts, 75° C., 300 psi, 5 min run time, 25 min hold time without stirring. The resulting mixture was passed through a silica gel column eluted with 5% acetone in chloroform to yield 180 mg (36.0%) of the benzoquinoline product as an enantiomeric mixture. $^1$H-NMR (300 MHz, DMSO-d6): δ 8.30 (brs, 1H) 7.86 (m, 1H), 7.24 (m, 2H), 1.0-3.5 (m, 14H).

8-Amino-7-thiophen-2-yl-1,2,3,4,4a,5,6,11b-octahydro-10-thia-11-aza-cyclopenta[b]phenanthrene-9-carboxylic acid amide (107)

To a solution of the above intermediate (180 mg, 0.55 mmol) in ethanol (5 ml) was added potassium carbonate (114 mg, 0.83 mmol) and 2-chloroacetamide (77.6 mg, 0.83 mmol). This solution was heated at 80° C. overnight with stirring. The resulting solution was evaporated to dryness and passed through a silica gel column eluted with 5% acetone in chloroform to yield 23.4 mg (11%) of the amino-carboxamide. This product was determined to be an enantiomeric mixture (55% and 42%) by analytical HPLC. ¹H-NMR (300 MHz, DMSO-d6): δ 8.30 (brs, 1H), 7.87 (d, J=5.1 Hz, 1H), 7.2 (m, 3H), 5.74 (brs, 1H), 1.0-3.5 (m, 14H).

Particularly Preferred Compounds

3-Amino-6-(2-benzoyloxy-ethyl)-4-thiophen-2-yl-6,7-dihydro-5H-1-thia-6,8-diaza-s-indacene-2-carboxylic acid amide
3-Amino-6-pyridin-3-ylmethyl-4-thiophen-2-yl-6,7-dihydro-5H-1-thia-6,8-diaza-s-indacene-2-carboxylic acid amide
3-Amino-4-thiophen-2-yl-5,6,7,8-tetrahydro-1-thia-7,9-diaza-cyclopenta[b]naphthalene-2-carboxylic acid amide
3-Amino-7-ethoxy-4-thiophen-2-yl-6,7-dihydro-5H-cyclopenta[b]thieno[3,2-e]pyridine-2-carboxylic acid amide
3-Amino-7-methyl-4-thiophen-2-yl-6,7-dihydro-5H-cyclopenta[b]thieno[3,2-e]pyridine-2-carboxylic acid amide
3-Amino-7-[(2-hydroxy-2-phenyl-ethylcarbamoyl)-methyl]-4-thiophen-2-yl-6,7-dihydro-5H-cyclopenta[b]thieno[3,2-e]pyridine-2-carboxylic acid amide
3-Amino-8-(2-cyano-ethyl)-4-thiophen-2-yl-5,6,7,8-tetrahydro-thieno[2,3-b]quinoline-2-carboxylic acid amide
3-Amino-8-methoxy-4-thiophen-2-yl-5,6,7,8-tetrahydro-thieno[2,3-b]quinoline-2-carboxylic acid amide
3-Amino-4-(3-methyl-thiophen-2-yl)-5-oxo-5,6,7,8-tetrahydro-thieno[2,3-b]quinoline-2-carboxylic acid amide
3-Amino-6-(4,5-dihydro-thiazol-2-yl)-4-thiophen-2-yl-6,7-dihydro-5H-1-thia-6,8-diaza-s-indacene-2-carboxylic acid amide Preferred Uses of Contemplated Compounds and Compositions Based on the unexpected discovery that numerous protein kinase inhibitors may be employed as antiviral agents, the inventors generally contemplate that known and novel kinase inhibitors may be used as antiviral drugs and vice versa—antiviral drugs as kinase inhibitors (e.g., in the treatment of diseases known to be associated with dysregulation of kinases, especially including neoplastic diseases). Thus, in one general aspect of the inventive subject matter, all known kinase inhibitors, and particularly those contemplated herein and/or involved in a signaling cascade may be employed as antiviral agents (and vice versa).

For example, various contemplated compounds exhibit IKKβ inhibitory activity and have been demonstrated by the inventors to be effective anti-HBV agents. However, it should be recognized that numerous other kinase inhibitors may also demonstrate an antiviral effect against a variety of viruses other than HBV, and especially contemplated alternative viruses include those in which the virus directly or indirectly interferes with the host cell's signal transduction, and/or in which the viral infection is associated with an inflammatory response of the host (e.g., HCV). Still further, it should be recognized that contemplated anti-HBV compounds may also be used as therapeutic agents against diseases associated with IKKβ dysregulation which may include, melanoma, mammary carcinoma, non-small cell lung carcinoma, colorectal carcinoma, squamous-cell carcinoma, leukemia, lymphoma, thyroid carcinoma, fibrosarcoma, pancreatic cancer, prostate cancer, multiple myeloma, ovarian cancer, rheumatoid arthritis, multiple sclerosis, psoriasis, or inflammatory disorders.

Therefore, the inventors especially contemplate pharmaceutical compositions in which contemplated kinase inhibitory compounds are present at a concentration effective to inhibit or reduce viral propagation in a patient's cell. The term "viral propagation" as used herein especially includes reduction of viral replication, synthesis, processing and/or assembly of viral polypeptides, viral entry into the host cell, and release of viral particles from an infected cell.

Contemplated Pharmaceutical Compositions

It is particularly preferred that contemplated compounds are included in a pharmaceutical composition that is formulated with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracistemally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrastemal, subcutaneous and intra-articular injection and infusion.

Pharmaceutical compositions for parenteral injection preferably comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and non-aqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

Contemplated compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like, Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes. The active compounds may also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions may also include adjuvants such as wetting agents, emulsifying and suspending agents, sweetening, flavoring, and perfuming agents.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to a compound of the present invention, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., *Methods in Cell Biology*, Volume XIV, Academic Press, New York, N.Y. (1976), p. 33 et seq.

The compounds of the present invention may be used in the form of pharmaceutically acceptable salts derived from inorganic or organic acids. By "pharmaceutically acceptable salt" is meant those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge, et al. describe pharmaceutically acceptable salts in detail in *J. Pharmaceutical Sciences*, 1977, 66: 1 et seq. The salts may be prepared in situ during the final isolation and purification of the compounds of the invention or separately by reacting a free base function with a suitable acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups may be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulfuric acid and phosphoric acid and such organic acids as oxalic acid, maleic acid, succinic acid and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like. Preferred salts of the compounds of the invention include phosphate, TRIS, and acetate.

Actual dosage levels of active ingredients in the pharmaceutical compositions of this invention may be varied so as to obtain an amount of the active compound(s) that is effective to achieve the desired therapeutic response for a particular patient, composition, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required to achieve the desired therapeutic effect and to gradually increase the dosage until the desired effect is achieved. Generally, dosage levels of about 1 to about 500, more preferably of about 5 to about 50 mg of an active compound per kilogram of body weight per day are administered orally to a mammalian patient. If desired, the effective daily dose may be divided into multiple doses for purposes of administration, e.g., two to four separate doses per day.

EXAMPLES

The following examples are provided to illustrate the inhibition of replication of IKKβ and HBV by compounds in the invention. However, it should be appreciated that numerous modifications of the compounds, assay, and virus may result in similarly beneficial results. Consequently, the examples below are given only to provide exemplary guidance to a practitioner.

IKKβ Cell-based Assay

A cell-based assay screening system using an NFκB-Luc cell line was designed to study IKKβ activity. The parental cell line of NFκB-Luc is the 293 human embryonic kidney cell line, which was transfected to express the firefly luciferase gene under the control of an NFκB responsive element. Treatment of NFκB-Luc cells with tumor necrosis alpha (TNFα) induces activation of IKKβ, leading to phosphorylation, ubiquitination and degradation of IκB, and the subsequent translocation of NFκB to the nucleus. Nuclear translocation of NFκB results in its ability to initiate gene transcription, which can be detected by the luciferase reporter system. Therefore, in this system, inhibition of IKKβ enzymatic activity is expected to result in inhibition of luciferase activity. For compound testing, 7500 NFκB-Luc cells were added per well of 384-well plates and incubated for 16 hours at 37° C. in a humidified incubator with 5% CO2. Cells were pre-incubated with various concentrations of compound diluted in MEM/10% FBS. After one hour, cells were treated with 20 ng/mL TNFα diluted in MEM/10% FBS. After a 4.5-hour incubation, cells were lysed and luciferase activity was measured. IKKβ inhibitory activity was calculated based on reduction of the luciferase signal and expressed as EC50 (effective concentration to reduce the luciferase signal by 50%).

IKKβ In Vitro Assay

For determination of IC50 values, an in vitro IKKβ assay was designed to study IKKβ enzymatic activity in a cell-free system. His-tagged human IKKβ expressed from a baculovirus construct in Sf9 insect cells and Glutathione S Transferase (GST)-IκBα fusion protein (IκBα residues 1 through 54) expressed in $E.$ $coli$ were purified and utilized in an in vitro radiolabel incorporation assay. The reaction contained 25 mM HEPES, pH 7.4, 50 mM NaCl, 1 mM MgCl2, 0.2 mM EDTA and 2.5 mM DTT. Purified IKKβ (100 nM) was pre-incubated with compound for 30 minutes at room temperature. The kinase reaction was initiated by adding 5 μM GST-IκBα substrate, 1 μM unlabeled ATP and 0.5 μCi $^{33}$P-γ-ATP. The reaction was allowed to proceed at room temperature for 60 minutes and terminated by the addition 100 μl 1% trichloroacetic acid (TCA). The reaction was transferred to a 96-well glass fiber filter plate previously blocked with 1% pyrophosphate. The filter plate was washed five times with water and twice with absolute ethanol and dried. Liquid scintillation cocktail was added to each well and radiolabel incorporation was quantified using the Packard TopCount HTS Scintillation Counter. Inhibition of IKKβ activity was calculated based on reduction of the radioactive signal and reported as IC50 (inhibitory concentration to reduce the signal by 50%).

HBV Screening Assay

HepG2 cells were transduced using a baculovirus to deliver the HBV genome essentially as previously described (Delaney et al. in Hepatology 1998; 28: 1134-1146). Transduced cells were cultured in supplemented EMEM media with 10% fetal bovine serum in a 5% CO2 incubator at 37° C. for three days in the presence of test compounds. The cells were lysed in a buffer containing 0.5% NP-40 and 500 mg/ml proteinase K. A solid-phase hybridization was performed to capture the viral DNA and to label the target DNA with Digoxigenin-labeled DNA probes. The viral DNA was detected by ELISA, using horseradish peroxidase-conjugated anti-digoxigenin antibodies.

The EC50 values were determined using ExcelFit software from the inhibition values of a titration curve for each compound. For CC50 determinations, the same titration of compounds was co-cultured with non-transduced HepG2 for three days under the conditions described above. The Promega CellTiter 96 Aqueous One Solution Cell Proliferation Assay was used to measure cell proliferation/viability. The CC50 values were determined using ExcelFit software from the inhibition values of the titration curve for each compound.

Test Results for Selected Contemplated Compounds

Table 1 below lists selected compounds with their structures and corresponding antiviral activity (EC50 in μM). Antiviral activity was determined using assays as described above. All tested compounds had a CC50 value of greater than 50,000 μM. ND means not determined. (Legend: A:<1 μM, B: 1-10 μM, C:>10 μM)

TABLE 1

| No. | Name | Structure | EC50 |
|---|---|---|---|
| 1 | 3-Amino-6-tert-butyloxycarbonyl-4-thiophen-2-yl-6,7-dihydro-5H-1-thia-6,8-diaza-s-indacene-2-carboxylic acid amide | 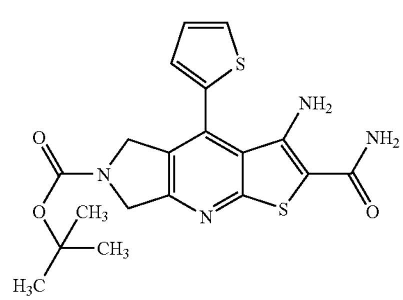 | C |

TABLE 1-continued

| No. | Name | Structure | EC50 |
|---|---|---|---|
| 2 | 3-Amino-4-thiophen-2-yl-6,7-dihydro-5H-1-thia-6,8-diaza-s-indacene-2-carboxylic acid amide | 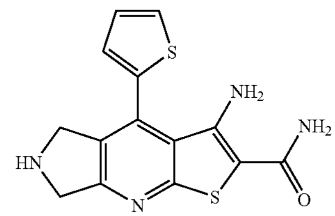 | B |
| 3 | 3-Amino-6-(3-chloro-propyl)-4-thiophen-2-yl-6,7-dihydro-5H-1-thia-6,8-diaza-s-indacene-2-carboxylic acid amide | 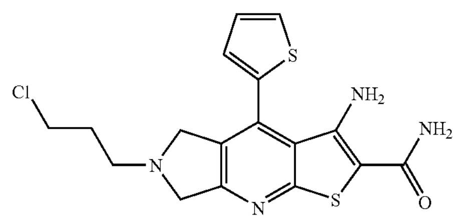 | B |
| 4 | 3-Amino-6-(tetrahydro-pyran-2-ylmethyl)-4-thiophen-2-yl-6,7-dihydro-5H-1-thia-6,8-diaza-s-indacene-2-carboxylic acid amide | 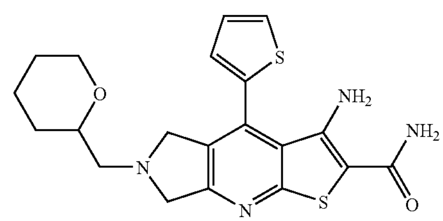 | C |
| 5 | 3-Amino-6-[5-(2-methoxy-phenyl)-[1,2,4]oxadiazol-3-ylmethyl]-4-thiophen-2-yl-6,7-dihydro-5H-1-thia-6,8-diaza-s-indacene-2-carboxylic acid amide | 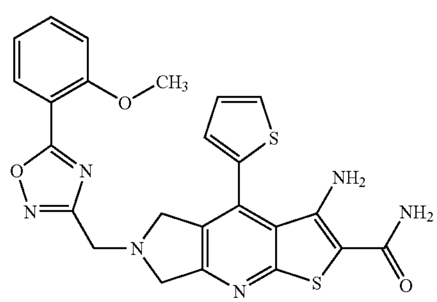 | B |
| 6 | 3-Amino-6-(3-methyl-butyl)-4-thiophen-2-yl-6,7-dihydro-5H-1-thia-6,8-diaza-s-indacene-2-carboxylic acid amide | 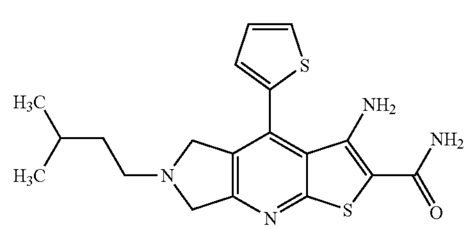 | C |
| 7 | 3-Amino-6-pyridin-2-ylmethyl-4-thiophen-2-yl-6,7-dihydro-5H-1-thia-6,8-diaza-s-indacene-2-carboxylic acid amide | 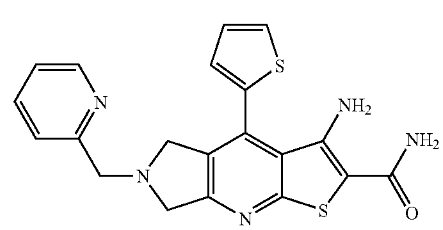 | C |

TABLE 1-continued

| No. | Name | Structure | EC50 |
|---|---|---|---|
| 8 | 3-Amino-6-cyclopropylmethyl-4-thiophen-2-yl-6,7-dihydro-5H-1-thia-6,8-diaza-s-indacene-2-carboxylic acid amide | 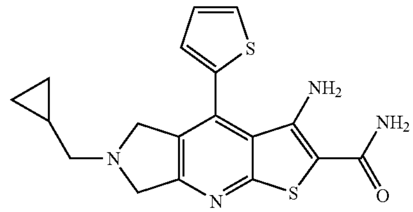 | C |
| 9 | 3-Amino-6-(2-benzoyloxy-ethyl)-4-thiophen-2-yl-6,7-dihydro-5H-1-thia-6,8-diaza-s-indacene-2-carboxylic acid amide | 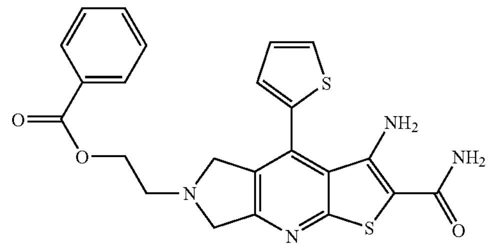 | B |
| 10 | 3-Amino-6-phenethyl-4-thiophen-2-yl-6,7-dihydro-5H-1-thia-6,8-diaza-s-indacene-2-carboxylic acid amide | 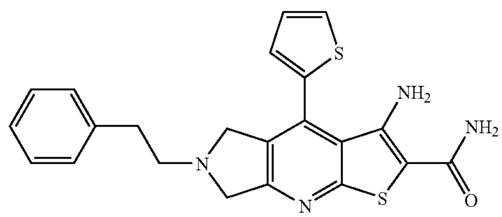 | C |
| 11 | 3-Amino-6-cyclohexylmethyl-4-thiophen-2-yl-6,7-dihydro-5H-1-thia-6,8-diaza-s-indacene-2-carboxylic acid amide | 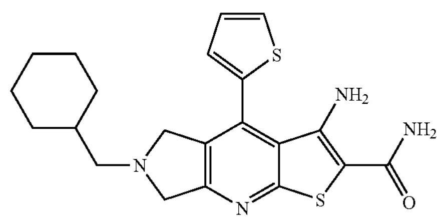 | B |
| 12 | 3-Amino-6-[2-(4-chloro-phenyl)-2-oxo-ethyl]-4-thiophen-2-yl-6,7-dihydro-5H-1-thia-6,8-diaza-s-indacene-2-carboxylic acid amide | 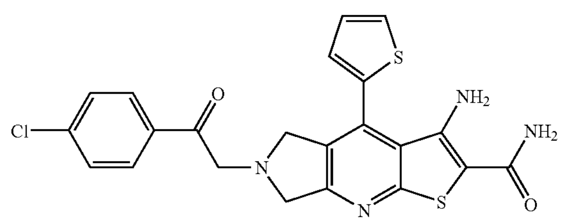 | B |
| 13 | 3-Amino-6-(3-hydroxy-2-methyl-propyl)-4-thiophen-2-yl-6,7-dihydro-5H--thia-6,8-diaza-s-indacene-2-carboxylic acid amide | 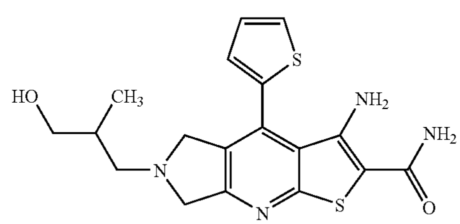 | B |
| 14 | 3-Amino-6-isobutyl-4-thiophen-2-yl-6,7-dihydro-5H-1-thia-6,8-diaza-s-indacene-2-carboxylic acid amide | 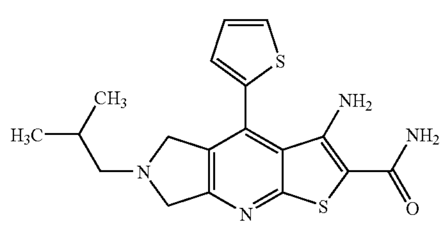 | C |

TABLE 1-continued

| No. | Name | Structure | EC50 |
|---|---|---|---|
| 15 | 3-Amino-6-(2-hydroxy-ethyl)-4-thiophen-2-yl-6,7-dihydro-5H-1-thia-6,8-diaza-s-indacene-2-carboxylic acid amide | 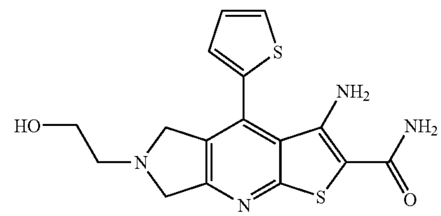 | B |
| 16 | 3-Amino-6-pentyl-4-thiophen-2-yl-6,7-dihydro-5H-1-thia-6,8-diaza-s-indacene-2-carboxylic acid amide | 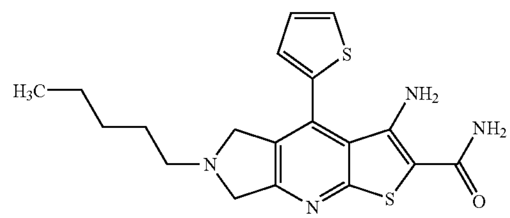 | C |
| 17 | 3-Amino-6-(2-methoxy-ethyl)-4-thiophen-2-yl-6,7-dihydro-5H-1-thia-6,8-diaza-s-indacene-2-carboxylic acid amide | 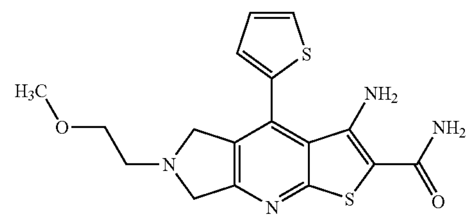 | C |
| 18 | 3-Amino-6-carbethoxymethyl-4-thiophen-2-yl-6,7-dihydro-5H-1-thia-6,8-diaza-s-indacene-2-carboxylic acid amide | 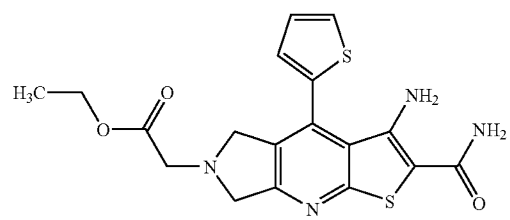 | C |
| 19 | 3-Amino-6-[2-(1,3-dioxo-1,3-dihydro-isoindol-2-yl)-ethyl]-4-thiophen-2-yl-6,7-dihydro-5H-1-thia-6,8-diaza-s-indacene-2-carboxylic acid amide | 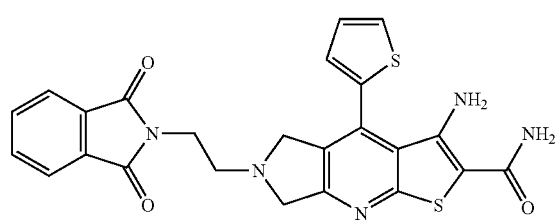 | C |
| 20 | 3-Amino-6-pyridin-3-ylmethyl-4-thiophen-2-yl-6,7-dihydro-5H-1-thia-6,8-diaza-s-indacene-2-carboxylic acid amide | 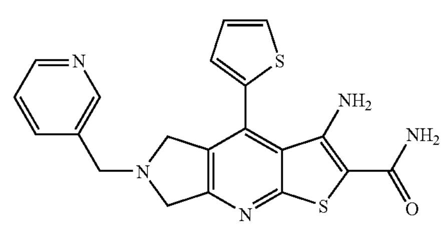 | A |
| 21 | 3-Amino-6-benzyl-4-thiophen-2-yl-6,7-dihydro-5H-1-thia-6,8-diaza-s-indacene-2-carboxylic acid amide | 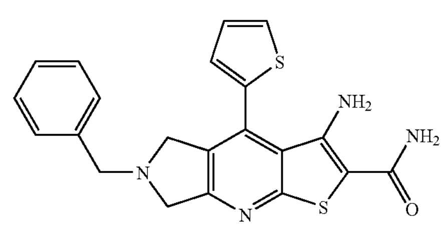 | B |

TABLE 1-continued

| No. | Name | Structure | EC50 |
|---|---|---|---|
| 22 | 3-Amino-6-(2-methyl-benzyl)-4-thiophen-2-yl-6,7-dihydro-5H-1-thia-6,8-diaza-s-indacene-2-carboxylic acid amide | 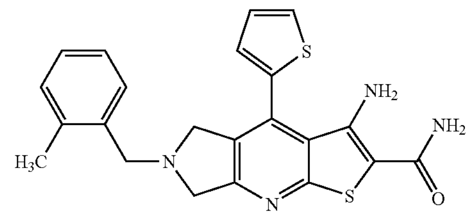 | B |
| 23 | 3-Amino-6-(3-fluoro-benzyl)-4-thiophen-2-yl-6,7-dihydro-5H-1-thia-6,8-diaza-s-indacene-2-carboxylic acid amide | 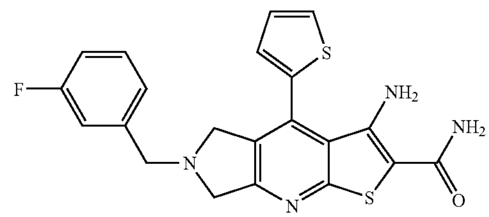 | C |
| 24 | 3-Amino-6-(3,5-dimethoxy-benzyl)-4-thiophen-2-yl-6,7-dihydro-5H-1-thia-6,8-diaza-s-indacene-2-carboxylic acid amide | 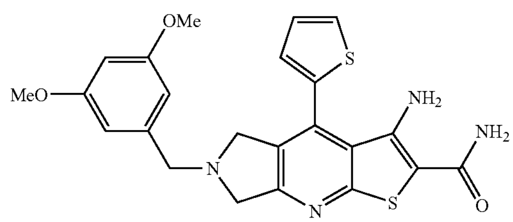 | C |
| 25 | 3-Amino-6-[3-(4-pyrimidin-2-yl-piperazin-1-yl)-propyl]-4-thiophen-2-yl-6,7-dihydro-5H-1-thia-6,8-diaza-s-indacene-2-carboxylic acid amide | 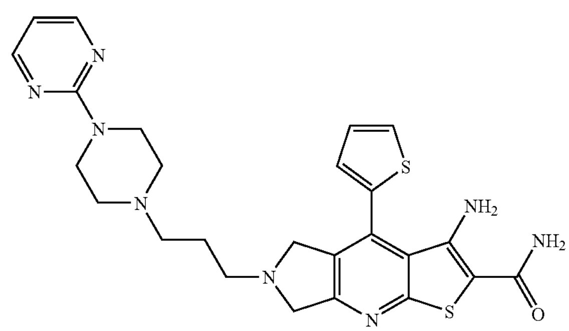 | C |
| 26 | 3-Amino-6-[3-(2-methoxy-piperidin-1-yl)-propyl]-4-thiophen-2-yl-6,7-dihydro-5H-1-thia-6,8-diaza-s-indacene-2-carboxylic acid amide | 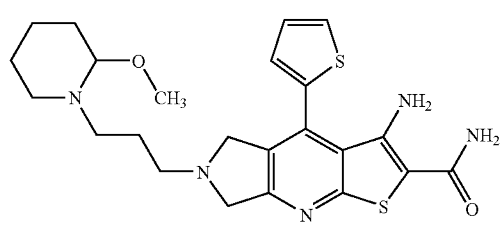 | C |
| 27 | 3-Amino-6-(3-morpholin-4-yl-propyl)-4-thiophen-2-yl-6,7-dihydro-5H-1-thia-6,8-diaza-s-indacene-2-carboxylic acid amide | 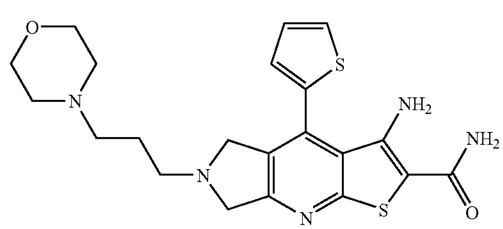 | C |

TABLE 1-continued

| No. | Name | Structure | EC50 |
|-----|------|-----------|------|
| 28 | 3-Amino-6-[3-(2-hydroxy-propylamino)-propyl]-4-thiophen-2-yl-6,7-dihydro-5H-1-thia-6,8-diaza-s-indacene-2-carboxylic acid amide | 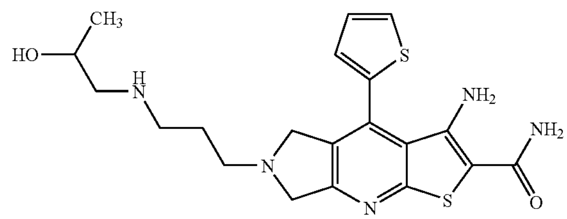 | C |
| 29 | 3-Amino-4-thiophen-2-yl-5,6,7,8-tetrahydro-1-thia-7,9-diaza-cyclopenta[b]naphthalene-2-carboxylic acid amide | 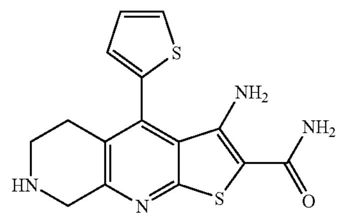 | A |
| 30 | 3-Amino-7-tert-butyloxycarbonyl-4-thiophen-2-yl-5,6,7,8-tetrahydro-1-thia-7,9-diaza-cyclopenta[b]naphthalene-2-carboxylic acid amide | 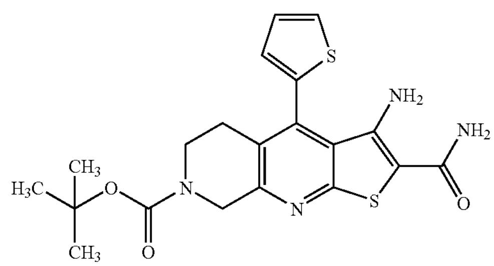 | C |
| 31 | 3-Amino-7-benzyl-4-thiophen-2-yl-5,6,7,8-tetrahydro-1-thia-7,9-diaza-cyclopenta[b]naphthalene-2-carboxylic acid amide | 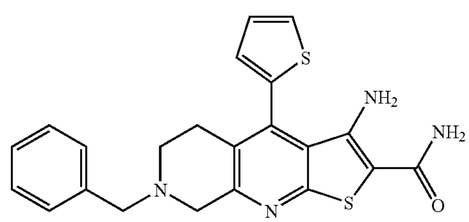 | ND |
| 32 | 3-Amino-6-tert-butyloxycarbonyl-4-thiophen-2-yl-5,6,7,8-tetrahydro-thieno[2,3-b][1,6]naphthyridine-2-carboxylic acid amide | 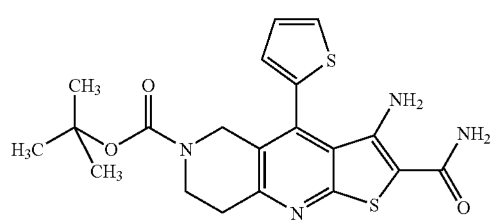 | C |
| 33 | 3-Amino-6-benzyl-4-(5-methyl-furan-2-yl)-5,6,7,8-tetrahydro-thieno[2,3-b][1,6]naphthyridine-2-carboxylic acid amide | 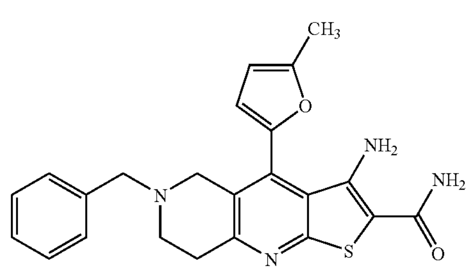 | C |

TABLE 1-continued

| No. | Name | Structure | EC50 |
|---|---|---|---|
| 34 | 6-Acetyl-3-amino-4-thiophen-2-yl-5,6,7,8-tetrahydro-thieno[2,3-b][1,6]naphthyridine-2-carboxylic acid amide | 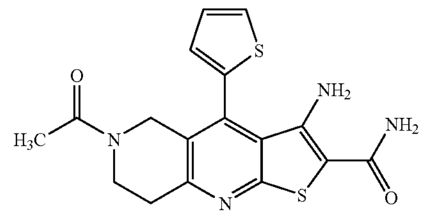 | C |
| 35 | 3-Amino-7-ethoxy-4-thiophen-2-yl-6,7-dihydro-5H-cyclopenta[b]thieno[3,2-e]pyridine-2-carboxylic acid amide | 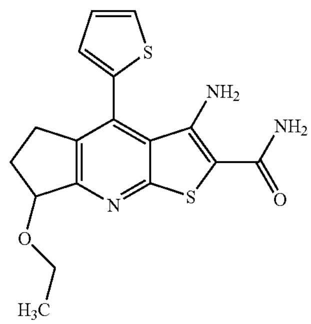 | A |
| 36 | 3-Amino-7-carboxymethyl-4-thiophen-2-yl-6,7-dihydro-5H-cyclopenta[b]thieno[3,2-e]pyridine-2-carboxylic acid amide | 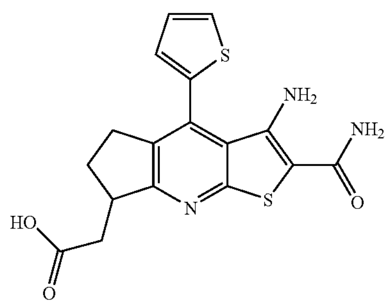 | C |
| 37 | 3-Amino-7-methyl-4-thiophen-2-yl-6,7-dihydro-5H-cyclopenta[b]thieno[3,2-e]pyridine-2-carboxylic acid amide | 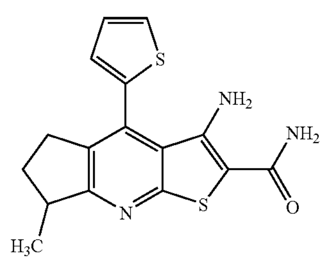 | A |
| 38 | 3-Amino-7-(2-morpholin-4-yl-2-oxo-ethyl)-4-thiophen-2-yl-6,7-dihydro-5H-cyclopenta[b]thieno[3,2-e]pyridine-2-carboxylic acid amide | 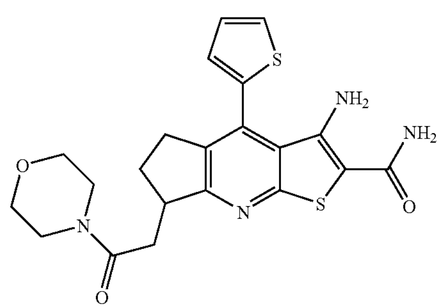 | C |

TABLE 1-continued

| No. | Name | Structure | EC50 |
|---|---|---|---|
| 39 | 3-Amino-7-[(2-hydroxy-2-phenyl-ethylcarbamoyl)-methyl]-4-thiophen-2-yl-6,7-dihydro-5H-cyclopenta[b]thieno[3,2-e]pyridine-2-carboxylic acid amide | 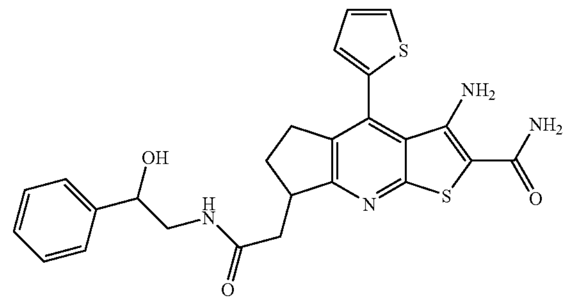 | C |
| 40 | 3-Amino-7-carbomethoxymethyl-4-thiophen-2-yl-6,7-dihydro-5H-cyclopenta[b]thieno[3,2-e]pyridine-2-carboxylic acid amide | 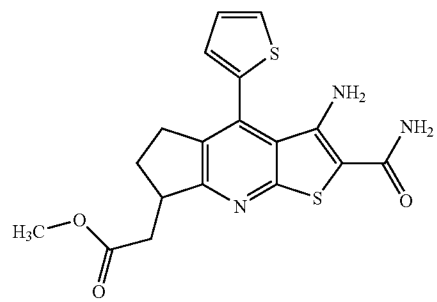 | C |
| 41 | 3-Amino-7-carbethoxymethyl-4-thiophen-2-yl-6,7-dihydro-5H-cyclopenta[b]thieno[3,2-e]pyridine-2-carboxylic acid amide | 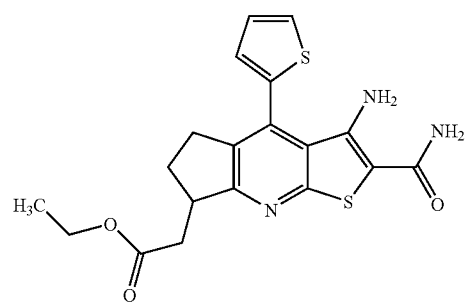 | C |
| 42 | 3-Amino-7-methylcarbamoylmethyl-4-thiophen-2-yl-6,7-dihydro-5H-cyclopenta[b]thieno[3,2-e]pyridine-2-carboxylic acid amide | 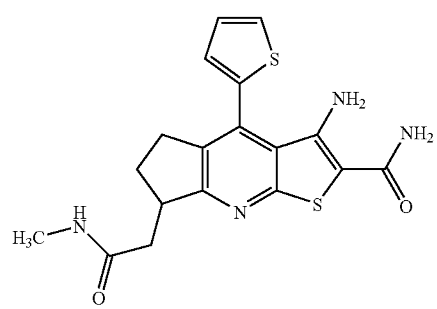 | B |
| 43 | 3-Amino-7-{[(5-methyl-furan-2-ylmethyl)-carbamoyl]-methyl}-4-thiophen-2-yl-6,7-dihydro-5H-cyclopenta[b]thieno[3,2-e]pyridine-2-carboxylic acid amide | 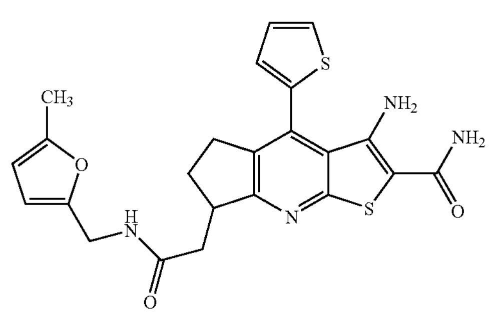 | C |

TABLE 1-continued

| No. | Name | Structure | EC50 |
|---|---|---|---|
| 44 | 3-Amino-7-[(2-methoxy-benzylcarbamoyl)-methyl]-4-thiophen-2-yl-6,7-dihydro-5H-cyclopenta[b]thieno[3,2-e]pyridine-2-carboxylic acid amide | 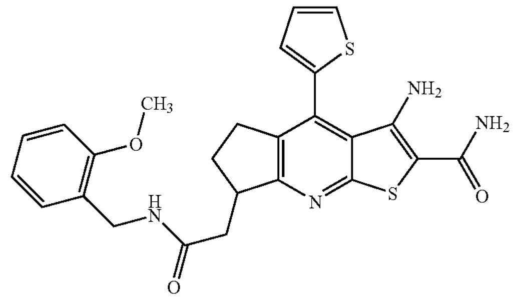 | C |
| 45 | 3-Amino-7-{[(pyridin-2-ylmethyl)-carbamoyl]-methyl}-4-thiophen-2-yl-6,7-dihydro-5H-cyclopenta[b]thieno[3,2-e]pyridine-2-carboxylic acid amide | 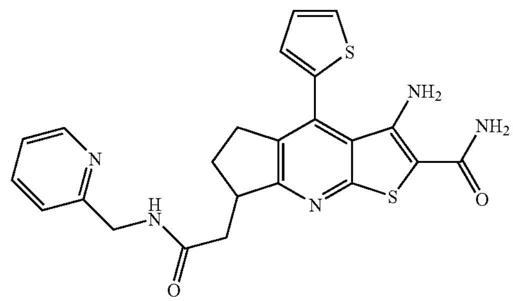 | C |
| 46 | 3-Amino-7-[(2-pyridin-2-yl-ethylcarbamoyl)-methyl]-4-thiophen-2-yl-6,7-dihydro-5H-cyclopenta[b]thieno[3,2-e]pyridine-2-carboxylic acid amide | 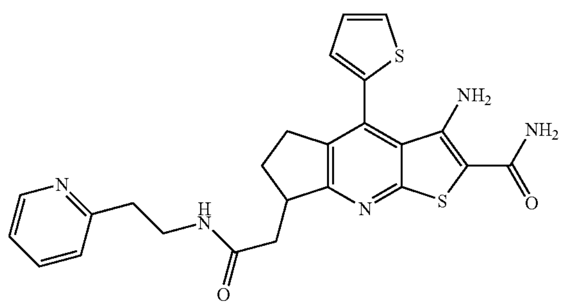 | C |
| 47 | 3-Amino-4-thiophen-2-yl-7-[(4-trifluoromethyl-benzylcarbamoyl)-methyl]-6,7-dihydro-5H-cyclopenta[b]thieno[3,2-e]pyridine-2-carboxylic acid amide | 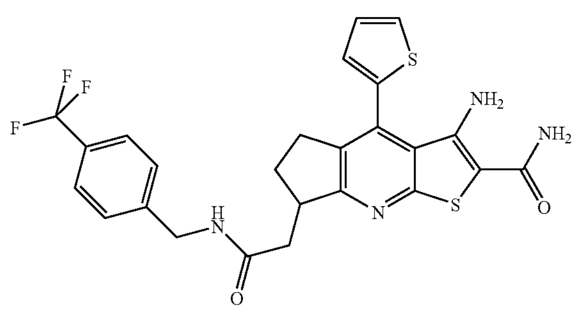 | C |
| 48 | 3-Amino-7-[(3-methyl-butylcarbamoyl)-methyl]-4-thiophen-2-yl-6,7-dihydro-5H-cyclopenta[b]thieno[3,2-e]pyridine-2-carboxylic acid amide | 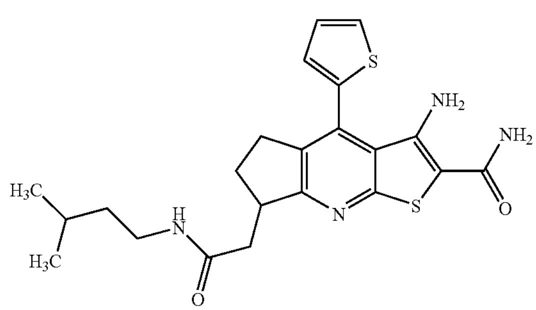 | C |

TABLE 1-continued

| No. | Name | Structure | EC50 |
|---|---|---|---|
| 49 | 3-Amino-7-dimethylcarbamoylmethyl-4-thiophen-2-yl-6,7-dihydro-5H-cyclopenta[b]thieno[3,2-e]pyridine-2-carboxylic acid amide | 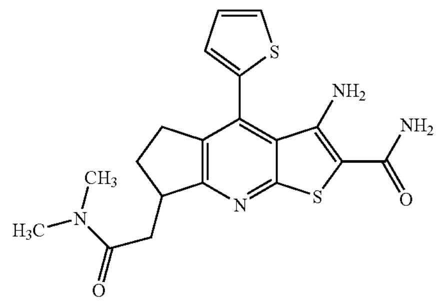 | C |
| 50 | 3-Amino-7-cyclobutylcarbamoylmethyl-4-thiophen-2-yl-6,7-dihydro-5H-cyclopenta[b]thieno[3,2-e]pyridine-2-carboxylic acid amide | 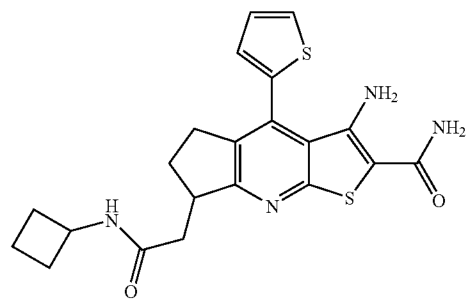 | C |
| 51 | 3-Amino-7-cyclohexylcarbamoylmethyl-4-thiophen-2-yl-6,7-dihydro-5H-cyclopenta[b]thieno[3,2-e]pyridine-2-carboxylic acid amide | 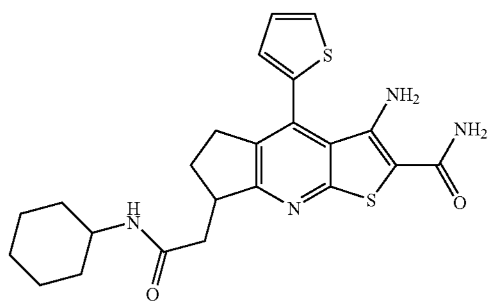 | C |
| 52 | 3-Amino-7-[2-(4-hydroxy-piperidin-1-yl)-2-oxo-ethyl]-4-thiophen-2-yl-6,7-dihydro-5H-cyclopenta[b]thieno[3,2-e]pyridine-2-carboxylic acid amide | 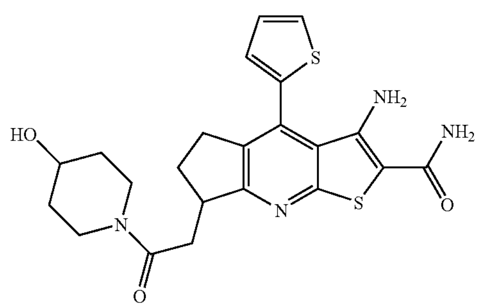 | C |
| 53 | 3-Amino-7-[2-oxo-2-(4-pyridin-2-yl-piperazin-1-yl)-ethyl]-4-thiophen-2-yl-6,7-dihydro-5H-cyclopenta[b]thieno[3,2-e]pyridine-2-carboxylic acid amide | 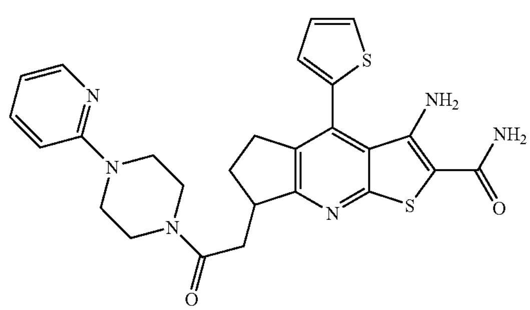 | C |

TABLE 1-continued

| No. | Name | Structure | EC50 |
|---|---|---|---|
| 54 | 4-[2-(3-Amino-2-carbamoyl-4-thiophen-2-yl-6,7-dihydro-5H-cyclopenta[b]thieno[3,2-e]pyridin-7-yl)-acetylamino]-piperidine-1-carboxylic acid ethyl ester | 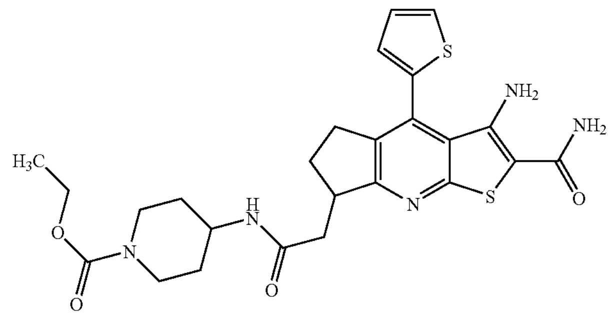 | C |
| 55 | 3-Amino-7-{[2-(1-methyl-pyrrolidin-2-yl)-ethylcarbamoyl]-methyl}-4-thiophen-2-yl-6,7-dihydro-5H-cyclopenta[b]thieno[3,2-e]pyridine-2-carboxylic acid amide | 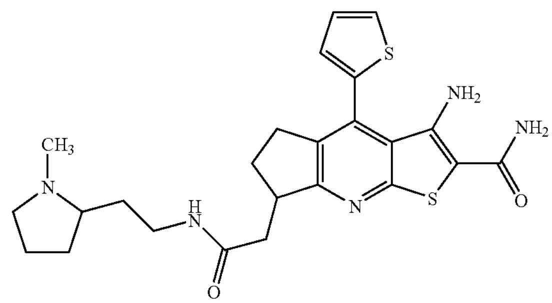 | C |
| 56 | 1-[2-(3-Amino-2-carbamoyl-4-thiophen-2-yl-6,7-dihydro-5H-cyclopenta[b]thieno[3,2-e]pyridin-7-yl)-acetyl]-piperidine-4-carboxylic acid ethyl ester | 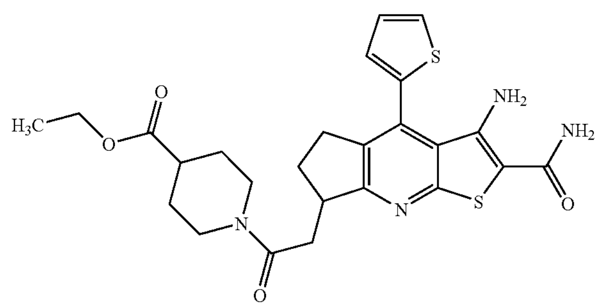 | C |
| 57 | 3-Amino-7-[(3-morpholin-4-yl-propylcarbamoyl)-methyl]-4-thiophen-2-yl-6,7-dihydro-5H-cyclopenta[b]thieno[3,2-e]pyridine-2-carboxylac acid amide | 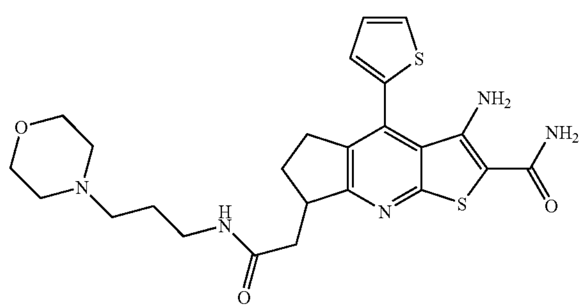 | C |
| 58 | 3-Amino-7-{[3-(2-methyl-piperidin-1-yl)-propylcarbamoyl]-methyl}-4-thiophen-2-yl-6,7-dihydro-5H-cyclopenta[b]thieno[3,2-e]pyridine-2-carboxyllc acid amide | 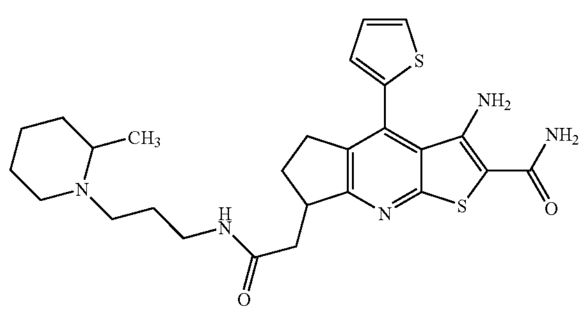 | C |

TABLE 1-continued

| No. | Name | Structure | EC50 |
|---|---|---|---|
| 59 | 3-Amino-7-hexyl-4-thiophen-2-yl-6,7-dihydro-5H-cyclopenta[b]thieno[3,2-e]pyridine-2-carboxylic acid amide | 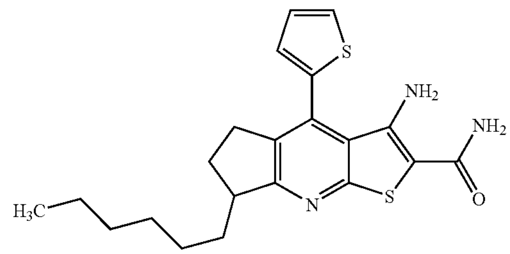 | C |
| 60 | 3-Amino-7-heptyl-4-thiophen-2-yl-6,7-dihydro-5H-cyclopenta[b]thieno[3,2-e]pyridine-2-carboxylic acid amide | 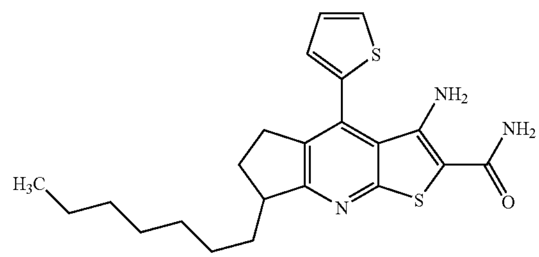 | C |
| 61 | 3-Amino-7-cyclopentyl-4-thiophen-2-yl-6,7-dihydro-5H-cyclopenta[b]thieno[3,2-e]pyridine-2-carboxylic acid amide | 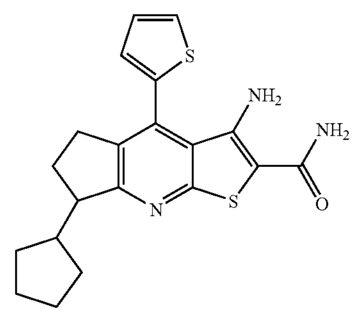 | B |
| 62 | 3-Amino-8-(2-cyano-ethyl)-4-thiophen-2-yl-5,6,7,8-tetrahydro-thieno[2,3-b]quinoline-2-carboxylic acid amide | 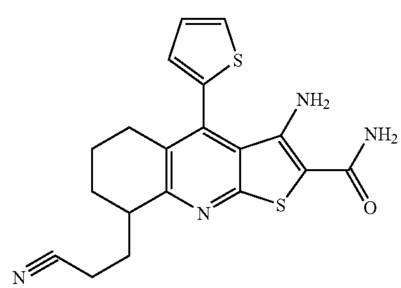 | C |
| 63 | 3-Amino-8-isobutyl-4-thiophen-2-yl-5,6,7,8-tetrahydro-thieno[2,3-b]quinoline-2-carboxylic acid amide | 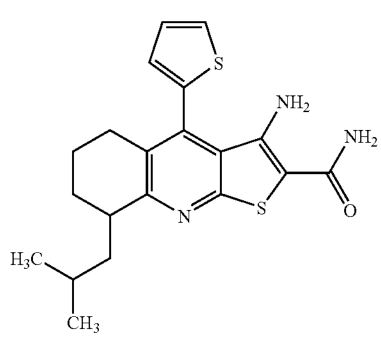 | B |

TABLE 1-continued

| No. | Name | Structure | EC50 |
|---|---|---|---|
| 64 | 3-Amino-8-benzyl-4-thiophen-2-yl-5,6,7,8-tetrahydro-thieno[2,3-b]quinoline-2-carboxylic acid amide | 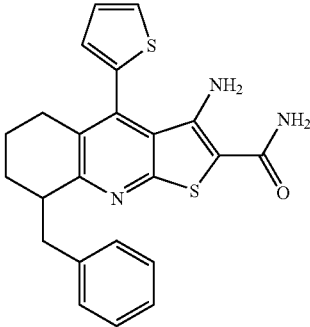 | C |
| 65 | 3-Amino-8-propyl-4-thiophen-2-yl-5,6,7,8-tetrahydro-thieno[2,3-b]quinoline-2-carboxylic acid amide | 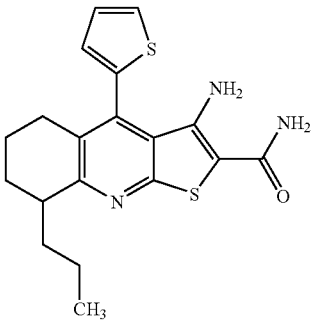 | B |
| 66 | 3-Amino-8-phenyl-4-thiophen-2-yl-5,6,7,8-tetrahydro-thieno[2,3-b]quinoiine-2-carboxylic acid amide | 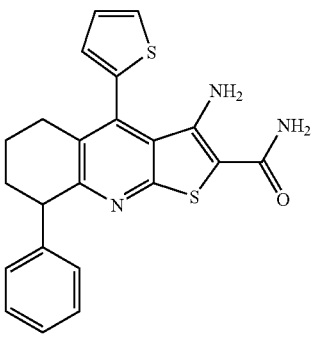 | B |
| 67 | 3-Amino-8-(3-methoxy-phenyl)-4-thiophen-2-yl-5,6,7,8-tetrahydro-thieno[2,3-b]quinoiine-2-carboxylic acid amide | 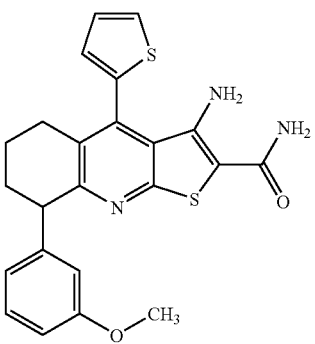 | C |

TABLE 1-continued

| No. | Name | Structure | EC50 |
|---|---|---|---|
| 68 | 3-Amino-8-cyclohexyl-4-thiophen-2-yl-5,6,7,8-tetrahydro-thieno[2,3-b]quinoline-2-carboxylic acid amide | 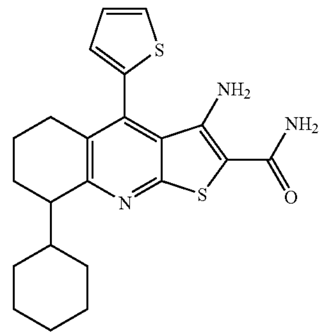 | C |
| 69 | 3-Amino-8-methoxy-4-thiophen-2-yl-5,6,7,8-tetrahydro-thieno[2,3-b]quinoline-2-carboxylic acid amide | 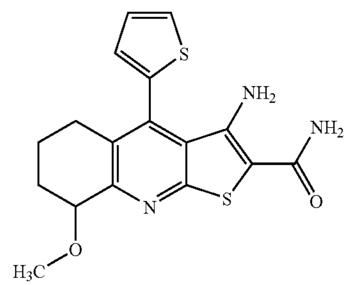 | A |
| 70 | 8-Allyl-3-amino-4-thiophen-2-yl-5,6,7,8-tetrahydro-thieno[2,3-b]quinoline-2-carboxylic acid amide | 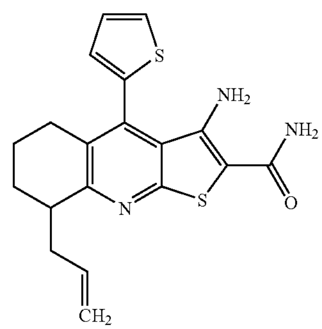 | B |
| 71 | 3-Amino-8-carbethoxymethyl-4-thiophen-2-yl-5,6,7,8-tetrahydro-thieno[2,3-b]quinoline-2-carboxylic acid amide | 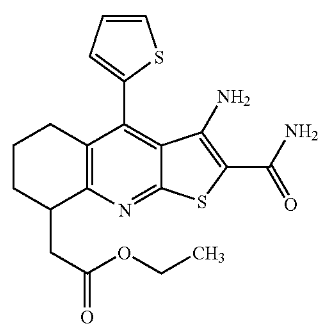 | C |
| 72 | 3-Amino-6-methyl-4-thiophen-2-yl-5,6,7,8-tetrahydro-thieno[2,3-b]quinoline-2-carboxylic acid amide | 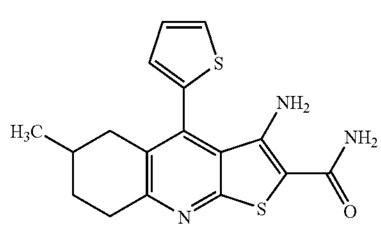 | C |

TABLE 1-continued

| No. | Name | Structure | EC50 |
|---|---|---|---|
| 73 | 3-Amino-6-ethyl-4-thiophen-2-yl-5,6,7,8-tetrahydro-thieno[2,3-b]quinoline-2-carboxylic acid amide | 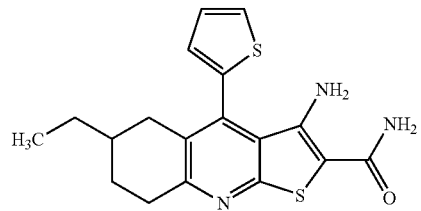 | C |
| 74 | 3-Amino-7-methyl-4-thiophen-2-yl-5,6,7,8-tetrahydro-thieno[2,3-b]quinoline-2-carboxylic acid amide | 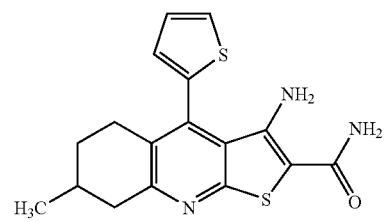 | C |
| 75 | 3-Amino-4-(3-methyl-thiophen-2-yl)-5-oxo-5,6,7,8-tetrahydro-thieno[2,3-b]quinoline-2-carboxylic acid amide | 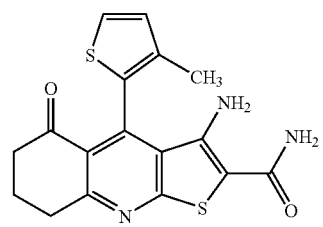 | A |
| 76 | 3-Amino-4-(thiophen-2-yl)-5-oxo-5,6,7,8-tetrahydro-thieno[2,3-b]quinoline-2-carboxylic acid amide | 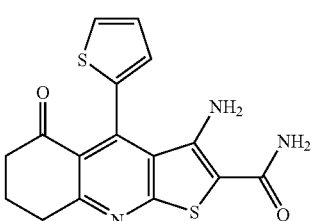 | B |
| 77 | 3-Amino-4-(4-chloro-phenyl)-5-oxo-5,6,7,8-tetrahydro-thieno[2,3-b]quinoline-2-carboxylic acid amide | 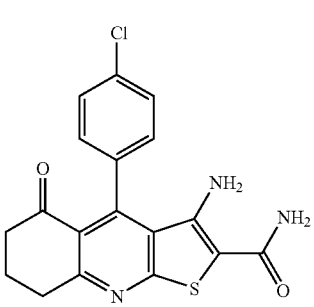 | C |
| 78 | 3-Amino-5-oxo-4-thiophen-2-yl-1,4,5,6,7,8-hexahydro-thiochromeno[2,3-b]pyrrole-2-carboxylic acid amide | 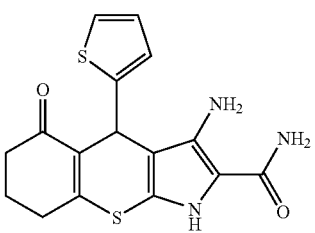 | C |

TABLE 1-continued

| No. | Name | Structure | EC50 |
|-----|------|-----------|------|
| 79 | 3-Amino-6-phenylthiocarbamoyl-4-thiophen-2-yl-6,7-dihydro-5H-1-thia-6,8-diaza-s-indacene-2-carboxylic acid amide | 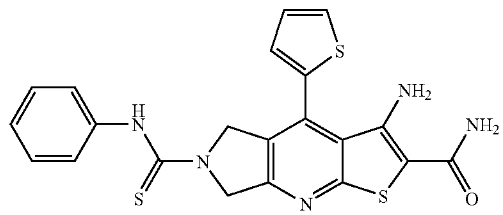 | C |
| 80 | 3-Amino-6-[(tetrahydro-furan-2-ylmethyl)-thiocarbamoyl]-4-thiophen-2-yl-6,7-dihydro-5H-1-thia-6,8-diaza-s-indacene-2-carboxylic acid amide | 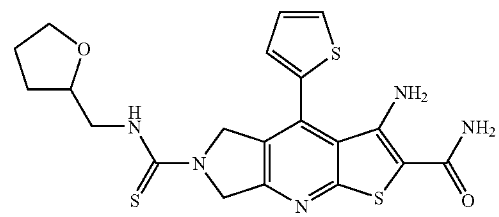 | C |
| 81 | 3-Amino-6-cyclopentylthiocarbamoyl-4-thiophen-2-yl-6,7-dihydro-5H-1-thia-6,8-diaza-s-indacene-2-carboxylic acid amide | 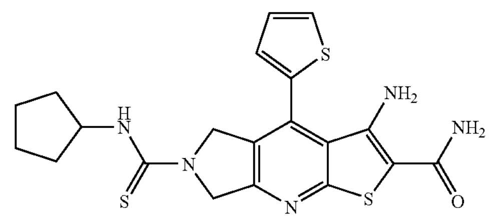 | B |
| 82 | 3-Amino-6-butylthiocarbamoyl-4-thiophen-2-yl-6,7-dihydro-5H-1-thia-6,8-diaza-s-indacene-2-carboxylic acid amide | 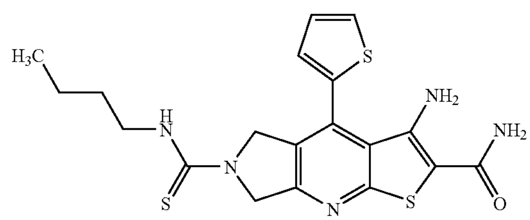 | B |
| 83 | 3-Amino-4-thiophen-2-yl-6-p-tolylthiocarbamoyl-6,7-dihydro-5H-1-thia-6,8-diaza-s-indacene-2-carboxylic acid amide | 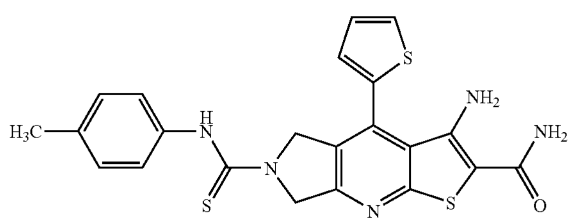 | C |
| 84 | 3-Amino-6-benzylthiocarbamoyl-4-thiophen-2-yl-6,7-dihydro-5H-1-thia-6,8-diaza-s-indacene-2-carboxylic acid amide | 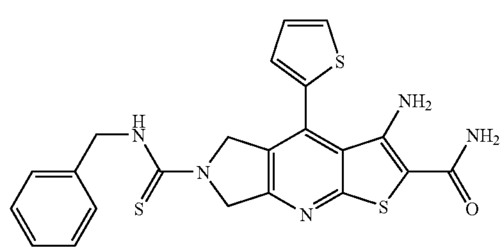 | B |
| 85 | 3-Amino-6-(3-methoxy-phenylthiocarbamoyl)-4-thiophen-2-yl-6,7-dihydro-5H-1-thia-6,8-diaza-s-indacene-2-carboxylic acid amide | 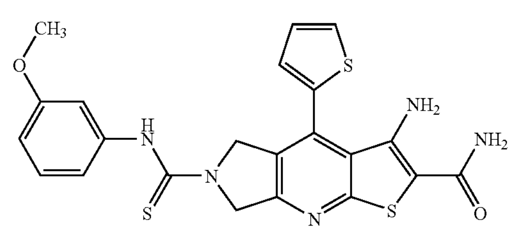 | C |

TABLE 1-continued

| No. | Name | Structure | EC50 |
|---|---|---|---|
| 86 | 3-Amino-6-(3-phenyl-propylthiocarbamoyl)-4-thiophen-2-yl-6,7-dihydro-5H-1-thia-6,8-diaza-s-indacene-2-carboxylic acid amide | 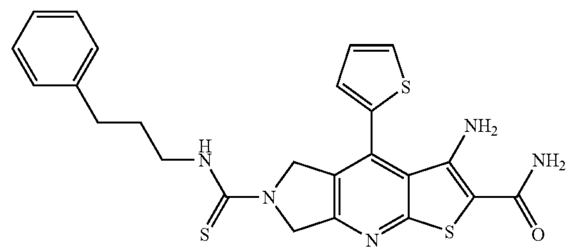 | B |
| 87 | 3-Amino-4-thiophen-2-yl-6-(3-trifluoromethyl-phenylthiocarbamoyl)-6,7-dihydro-5H-1-thia-6,8-diaza-s-indacene-2-carboxylic acid amide | 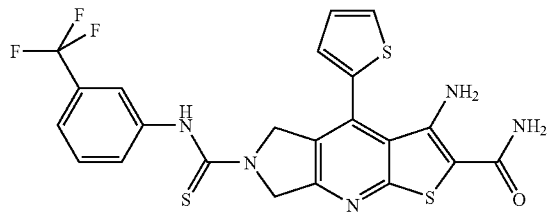 | C |
| 88 | 3-Amino-6-(4-fluoro-phenylthiocarbamoyl)-4-thiophen-2-yl-6,7-dihydro-5H-1-thia-6,8-diaza-s-indacene-2-carboxylic acid amide | 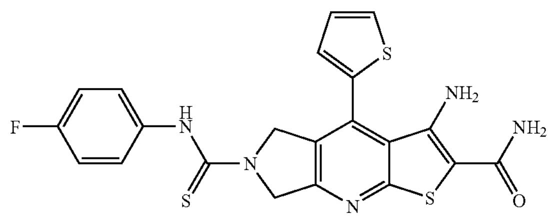 | C |
| 89 | 3-Amino-6-(3,5-dichloro-phenylthiocarbamoyl)-4-thiophen-2-yl-6,7-dihydro-5H-1-thia-6,8-diaza-s-indacene-2-carboxylic acid amide | 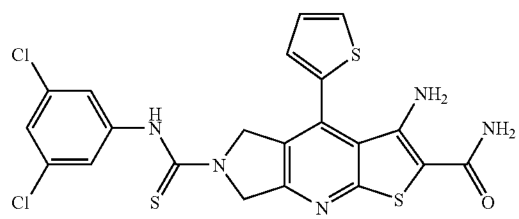 | C |
| 90 | 4-[(3-Amino-2-carbamoyl-4-thiophen-2-yl-5,7-dihydro-1-thia-6,8-diaza-s-indacene-6-carbothioyl)-amino]-benzoic acid methyl ester | 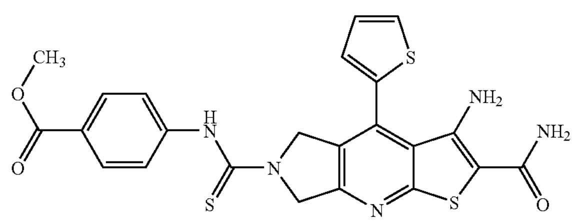 | C |
| 91 | 3-Amino-6-cyclopropylthiocarbamoyl-4-thiophen-2-yl-6,7-dihydro-5H-1-thia-6,8-diaza-s-indacene-2-carboxylic acid amide | 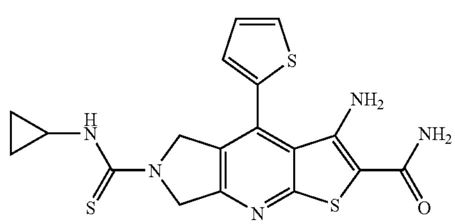 | B |
| 92 | 3-Amino-6-(3,5-dimethyl-phenylthiocarbamoyl)-4-thiophen-2-yl-6,7-dihydro-5H-1-thia-6,8-diaza-s-indacene-2-carboxylic acid amide | 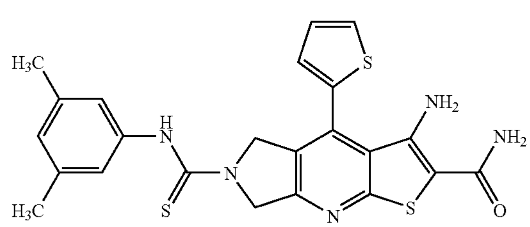 | C |

TABLE 1-continued

| No. | Name | Structure | EC50 |
|---|---|---|---|
| 93 | 3-Amino-6-(2-morpholin-4-yl-ethylthiocarbamoyl)-4-thiophen-2-yl-6,7-dihydro-5H-1-thia-6,8-diaza-s-indacene-2-carboxylic acid amide | 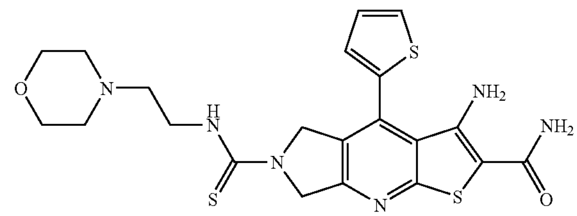 | C |
| 94 | 3-Amino-6-(3-morpholin-4-yl-propylthiocarbamoyl)-4-thiophen-2-yl-6,7-dihydro-5H-1-thia-6,8-diaza-s-indacene-2-carboxylic acid amide | 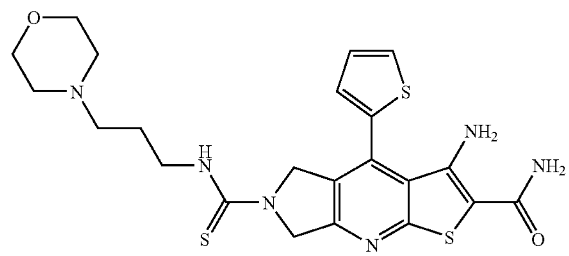 | C |
| 95 | 3-Amino-6-(4,5-dihydro-thiazol-2-yl)-4-thiophen-2-yl-6,7-dihydro-5H-1-thia-6,8-diaza-s-indacene-2-carboxylic acid amide | 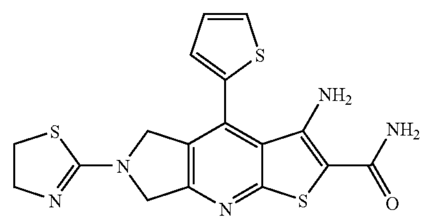 | A |
| 96 | 3-Amino-4-thiophen-2-yl-5,7-dihydro-1-thia-6,8-diaza-s-indacene-2,6-dicarboxylic acid 2-amide 6-phenylamide | 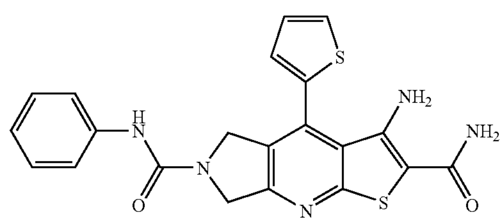 | C |
| 97 | 3-Amino-4-thiophen-2-yl-5,7-dihydro-1-thia-6,8-diaza-s-indacene-2,6-dicarboxylic acid 2-amide 6-benzylamide | 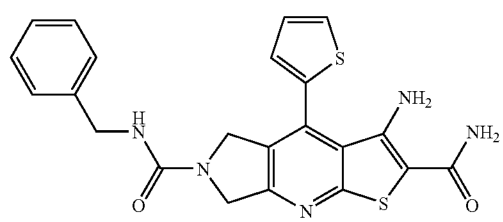 | C |
| 98 | 3-Amino-4-thiophen-2-yl-5,7-dihydro-1-thia-6,8-diaza-s-indacene-2,6-dicarboxylic acid 2-amide 6-ethylamide | 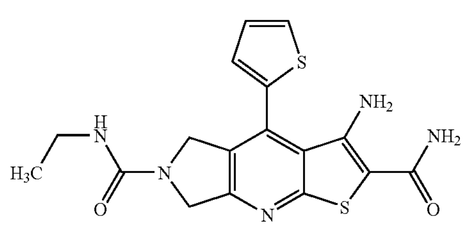 | A |

TABLE 1-continued

| No. | Name | Structure | EC50 |
|---|---|---|---|
| 99 | 3-Amino-4-thiophen-2-yl-5,7-dihydro-1-thia-6,8-diaza-s-indacene-2,6-dicarboxylic acid 2-amide 6-[(4-phenyl-piperazin-1-ylmethyl)-amide] | 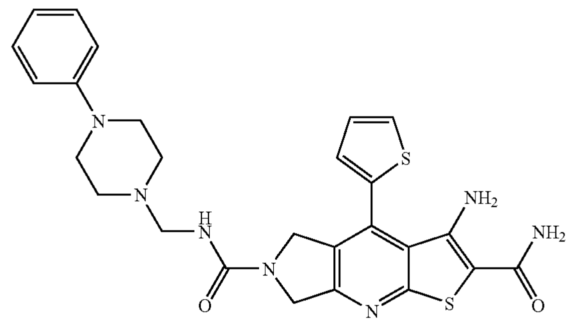 | C |
| 100 | 3-Amino-4-thiophen-2-yl-5,7-dihydro-1-thia-6,8-diaza-s-indacene-2,6-dicarboxylic acid 2-amide 6-thiophen-3-ylamide | 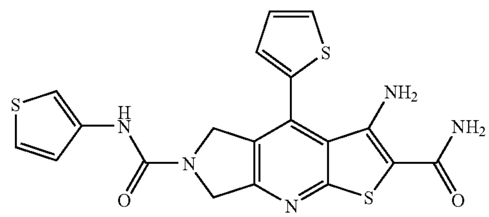 | A |
| 101 | 3-Amino-4-thiophen-2-yl-5,7-dihydro-1-thia-6,8-diaza-s-indacene-2,6-dicarboxylic acid 2-amide 6-cyclohexylamide | 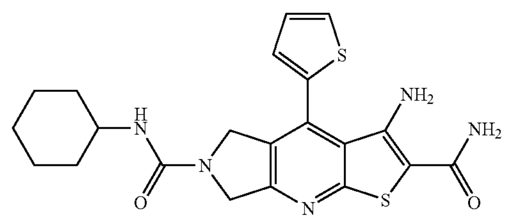 | C |
| 102 | 3-Amino-4-thiophen-2-yl-5,7-dihydro-1-thia-6,8-diaza-s-indacene-2,6-dicarboxylic acid 2-amide 6-[(6-morpholin-4-yl-pyridin-3-yl)-amide] | 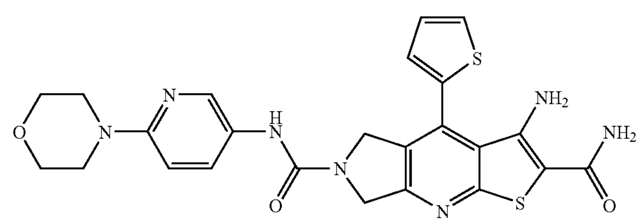 | C |
| 103 | 3-Amino-6-[2-(4-benzyl-cyclohexylamino)-acetyl]-4-thiophen-2-yl-6,7-dihydro-5H-1-thia-6,8-diaza-s-indacene-2-carboxylic acid amide | 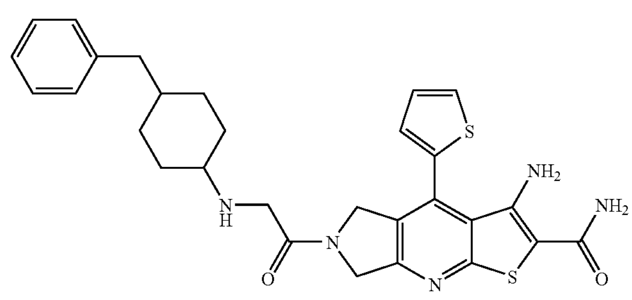 | B |
| 104 | 3-Amino-6-(2-chloro-acetyl)-4-thiophen-2-yl-6,7-dihydro-5H-1-thia-6,8-diaza-s-indacene-2-carboxylic acid amide | 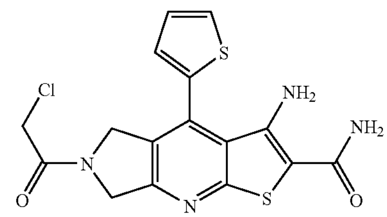 | B |

Thus, specific embodiments and applications of protein kinase inhibitors have been disclosed. It should be apparent, however, to those skilled in the art that many more modifications besides those already described are possible without departing from the inventive concepts herein. The inventive subject matter, therefore, is not to be restricted except in the spirit of the disclosure. Moreover, all terms employed herein should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. A compound of Formula I

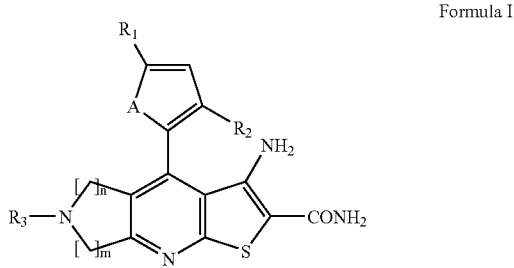

Formula I wherein A is S, O, or $N(CH_3)$;

$R_1$ and $R_2$ are, independently, H, $CH_3$, $CF_3$, or $CH_3O$;

$R_3$ is H;

or $R_3$ is a 5- or 6-membered ring, said ring optionally containing one or more double bonds, optionally containing 1-3 ring heteroatoms independently selected from O, N, and S, and optionally substituted with one or two groups independently selected from $CH_3$, $OCH_3$, $CO_2CH_3$, $OC(O)CH_3$, CN, and halo, wherein all methyl groups are optionally substituted with 1, 2, or 3 halogen atoms;

or $R_3$ is $C_{1-6}$ alkyl, $C_{1-6}$ alkanoyl, $C_{1-6}$ alkenyl, $C_{1-6}$ alkoxy, $C_{1-6}$ alkenoxy, wherein said alkyl groups, the alkyl moieties of said alkanoyl and said alkoxy groups, said alkenyl groups, and the alkenyl moieties of said alkenoxy groups may be straight-chain, branched, or cyclic, and can all optionally be substituted as follows:

a) with one, two, or three halogen atoms;

b) with one or two substituents independently selected from hydroxy, carboxyl, cyano, benzyl, benzoyl, and benzoyloxy;

c) with one saturated, unsaturated, or aromatic 5- or 6-membered ring containing 0-3 heteroatoms selected from N, O, and S, said ring optionally substituted with one or two groups independently selected from $CH_3$, $OCH_3$, $C(O)CH_3$, $CO_2CH_3$, $OC(O)CH_3$, CN, and halo, wherein all methyl groups are optionally substituted with 1, 2, or 3 halogen atoms; and d) with one group selected from $C_{1-6}$ alkanoyl, $C_{1-6}$ alkoxycarbonyl, $C_{1-6}$ alkylcarbamoyl, ethylcarbamoylmethyl, methylcarbamoylmethyl, 2-hydroxy-2-phenyl-ethylcarbamoylmethyl, or N-phthalimido;

or $R_3$ is $R_4NHC(O)$, $R_4NHC(S)$, or $R_4NHCH_2C(O)$, wherein $R_4$ is $C_{1-6}$ alkyl, wherein said alkyl group may be straight-chain, branched, or cyclic, and is optionally substituted as described for $R_3$ alkyl groups, or $R_4$ is a five- or 6-membered aromatic ring containing 0-3 heteroatoms independently selected from O, N, and S, all $R_4$ optionally substituted with one or two substituents independently selected from halo, methyl, and benzyl, wherein all rings are optionally substituted with one or two groups independently selected from $CH_3$, $OCH_3$, $CO_2CH_3$, $OC(O)CH_3$, CN, and halo, wherein all methyl groups are optionally substituted with 1, 2, or 3 halogen atoms;

and m and n are, independently, 1 or 2, provided that m and n are not both 2;

and further provided that when n=1, m=2, and $R_1$ and $R_2$ are both H, then $R_3$ is not methyl.

2. The compound of claim 1, wherein A is S, n is 1, m is 1, $R_1$ is H, and $R_2$ is H or $CH_3$.

3. The compound of claim 2, wherein $R_3$ is H or $C_{1-6}$ alkyl, optionally substituted with one or two substituents independently selected from halo, hydroxy, cyano, phenyl, pyridyl, benzoyl, benzoyl methyl, benzoyloxy, $C_{1-6}$ alkoxycarbonyl, $C_{1-6}$ alkylcarbamoyl, N-phthalimido, or $R_3$ is a 5- or 6-membered aromatic ring containing 1-3 heteroatoms independently selected from O, N, and S, wherein all rings are optionally substituted with one or two substituents independently selected from halo, $CH_3$, $CH_3O$, CN, $CF_3$, and $CH_3C(O)$, wherein all methyl groups are optionally substituted 1-3 chlorine atoms.

4. The compound of claim 3, wherein $R_3$ is $C_{1-4}$ alkyl, optionally monosubstituted with halogen, hydroxy, phenyl, benzyl, pyridyl, and pyridyl methyl, wherein the phenyl and pyridyl rings are optionally further monosubstituted with methyl or halogen.

5. The compound of claim 2, wherein $R_3$ is $R_4NHC(O)$, $R_4NHC(S)$, or $R_4NHCH_2C(O)$, wherein $R_4$ is $C_{1-6}$ alkyl, wherein said alkyl group may be straight-chain, branched, or cyclic, and is optionally substituted as described for $R_3$ alkyl groups, or $R_4$ is a five- or 6-membered aromatic ring containing 0-3 heteroatoms independently selected from O, N, and S, all $R_4$ optionally substituted with one or two substituents independently selected from halo, methyl, and benzyl, wherein all rings are optionally substituted with one or two groups independently selected from $CH_3$, $OCH_3$, $CO_2CH_3$, $OC(O)CH_3$, CN, and halo, wherein all methyl groups are optionally substituted with 1, 2, or 3 halogen atoms.

6. The compound of claim 1, wherein A is S, n is 2, m is 1, $R_1$ is H, and $R_2$ is H or $CH_3$.

7. The compound of claim 6, wherein $R_3$ is H or $C_{1-4}$ alkyl.

8. The compound of claim 1, wherein A is O, n is 1, m is 1, $R_1$ is H, and $R_2$ is H or $CH_3$.

9. The compound of claim 8, wherein $R_3$ is H or $C_{1-6}$ alkyl, optionally substituted with one or two substituents independently selected from halo, hydroxy, cyano, phenyl, pyridyl, benzoyl, benzoyl methyl, benzoyloxy, $C_{1-6}$ alkoxycarbonyl, $C_{1-6}$ alkylcarbamoyl, N-phthalimido, or $R_3$ is a 5- or 6-membered aromatic ring containing 1-3 heteroatoms independently selected from O, N, and S, wherein all rings are optionally substituted with one or two substituents independently selected from halo, $CH_3$, $CH_3O$, CN, $CF_3$, and $CH_3C(O)$, wherein all methyl groups are optionally substituted 1-3 chlorine atoms.

10. The compound of claim 9, wherein $R_3$ is $C_{1-4}$ alkyl, optionally monosubstituted with halogen, hydroxy, phenyl, benzyl, pyridyl, and pyridyl methyl, wherein the phenyl and pyridyl rings are optionally further monosubstituted with methyl or halogen.

11. The compound of claim 8, wherein $R_3$ is $R_4NHC(O)$, $R_4NHC(S)$, or $R_4NHCH_2C(O)$, wherein $R_4$ is $C_{1-6}$ alkyl, wherein said alkyl group may be straight-chain, branched, or cyclic, and is optionally substituted as described for $R_3$ alkyl groups, or $R_4$ is a five- or 6-membered aromatic ring containing 0-3 heteroatoms independently selected from O, N, and S, all $R_4$ optionally substituted with one or two substituents independently selected from halo, methyl, and benzyl, wherein all rings are optionally substituted with one or two groups independently selected from $CH_3$, $OCH_3$, $CO_2CH_3$, $OC(O)CH_3$, CN, and halo, wherein all methyl groups are optionally substituted with 1, 2, or 3 halogen atoms.

12. A compound of Formula II

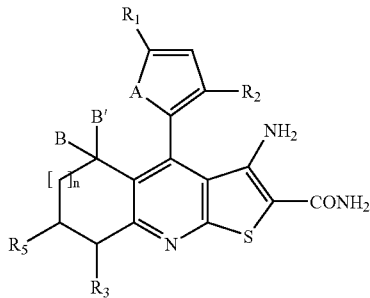

Formula II wherein n is zero, 1, 2, or 3; A is S, O, or $N(CH_3)$;

B and B' are either both H or jointly oxo;

$R_1$ and $R_2$ are, independently, H, $CH_3$, $CF_3$, or $CH_3O$;

$R_3$ is H;

or $R_3$ is a 5- or 6-membered ring, said ring optionally containing one or more double bonds, optionally containing 1-3 ring heteroatoms independently selected from O, N, and S, and optionally substituted with one or two groups independently selected from $CH_3$, $OCH_3$, $CO_2CH_3$, $OC(O)CH_3$, CN, and halo, wherein all methyl groups are optionally substituted with 1, 2, or 3 halogen atoms;

or $R_3$ is $C_{1-6}$ alkyl, $C_{1-6}$ alkanoyl, $C_{1-6}$ alkenyl, $C_{1-6}$ alkoxy, $C_{1-6}$ alkenoxy, wherein said alkyl groups, the alkyl moieties of said alkanoyl and said alkoxy groups, said alkenyl groups, and the alkenyl moieties of said alkenoxy groups may be straight-chain, branched, or cyclic, and may optionally be substituted as follows:

a) with one, two, or three halogen atoms;

b) with one or two substituents independently selected from hydroxy, carboxyl, cyano, benzyl, benzoyl, and benzoyloxy;

c) with one saturated, unsaturated, or aromatic 5- or 6-membered ring containing 0-3 heteroatoms selected from N, O, and S, said ring optionally substituted with one or two groups independently selected from $CH_3$, $OCH_3$, $C(O)CH_3$, $CO_2CH_3$, $OC(O)CH_3$, CN, and halo, wherein all methyl groups are optionally substituted with 1, 2, or 3 halogen atoms; and d) with one group selected from $C_{1-6}$ alkanoyl, $C_{1-6}$ alkoxycarbonyl, $C_{1-6}$ alkylcarbamoyl, ethylcarbamoylmethyl methylcarbamoylmethyl, 2-hydroxy-2-phenyl-ethylcarbamoylmethyl, or N-phthalimido;

or $R_3$ is $R_4NHC(O)$, $R_4NHC(S)$, or $R_4NHCH_2C(O)$, wherein $R_4$ is $C_{1-6}$ alkyl, wherein said alkyl group may be straight-chain, branched, or cyclic, and is optionally substituted as described for $R_3$ alkyl groups, or $R_4$ is a five- or 6-membered aromatic ring containing 0-3 heteroatoms independently selected from O, N, and S, all $R_4$ optionally substituted with one or two substituents independently selected from halo, methyl, and benzyl, wherein all rings are optionally substituted with one or two groups independently selected from $CH_3$, $OCH_3$, $CO_2CH_3$, $OC(O)CH_3$, CN, and halo, wherein all methyl groups are optionally substituted with 1, 2, or 3 halogen atoms; and $R_5$ is H or $C_3$ alkyl; or $R_3$ and $R_5$, together with the ring carbon atoms to which they are attached, form an additional fused 5- or 6-membered cycloalkyl group;

provided that when A is O or S, then $R_1$, $R_2$, $R_3$, B, and B' are not all H, and further provided that when A is S and $R_1$ is methyl, then $R_2$, $R_3$, B, and B' are not all H.

13. A compound according to claim 12, wherein A is S, $R_5$ is H; and wherein $R_3$ is selected from H, $C_{1-4}$ alkyl, $C_{1-4}$ alkenyl, or $C_{1-6}$ alkoxy, wherein said alkyl groups, the alkyl moieties of said alkoxy groups, and said alkenyl groups may be straight-chain, branched, or cyclic, and are optionally substituted with one or two substituents independently selected from halo, hydroxy, ethylcarbamoylmethyl methylcarbamoylmethyl, 2-hydroxy-2-phenyl-ethylcarbamoylmethyl, benzoyl, benzoyloxy, and a 5- or 6-membered ring, said ring optionally containing one or more double bonds, optionally containing 1-3 ring heteroatoms independently selected from O, N, and S, and optionally substituted with, independently, one or two groups independently selected from $CH_3$, $OCH_3$, $CF_3$, and halo;

and n=0, 1, or 2.

14. The compound of claim 13, wherein n=1 or 2, and $R_3$ is hydrogen, methyl, methoxy, ethoxy, or allyl.

15. A method of treating an HBV infection, comprising administering to a person in need of treatment thereof a therapeutically effective amount of a compound of Formula I or a compound of formula II, where formula I is

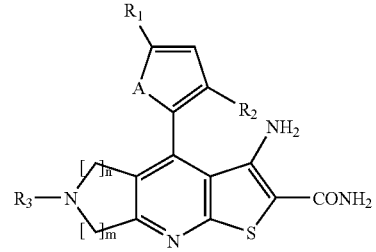

Formula I wherein A is S, O, or $N(CH_3)$;

$R_1$ and $R_2$ are, independently, H, $CH_3$, $CF_3$, or $CH_3O$;

$R_3$ is H;

or $R_3$ is a 5- or 6-membered ring, said ring optionally containing one or more double bonds, optionally containing 1-3 ring heteroatoms independently selected from O, N, and S, and optionally substituted with one or two groups independently selected from $CH_3$, $OCH_3$, $CO_2CH_3$, $OC(O)CH_3$, CN, and halo, wherein all methyl groups are optionally substituted with 1, 2, or 3 halogen atoms;

or $R_3$ is $C_{1-6}$ alkyl, $C_{1-6}$ alkanoyl, $C_{1-6}$ alkenyl, $C_{1-6}$ alkoxy, $C_{1-6}$ alkenoxy, wherein said alkyl groups, the alkyl moieties of said alkanoyl and said alkoxy groups, said alkenyl groups, and the alkenyl moieties of said alkenoxy groups may be straight-chain, branched, or cyclic, and can all optionally be substituted as follows:

a) with one, two, or three halogen atoms;

b) with one or two substituents independently selected from hydroxy, carboxyl, cyano, benzyl, benzoyl, and benzoyloxy;

c) with one saturated, unsaturated, or aromatic 5- or 6-membered ring containing 0-3 heteroatoms selected from N, O, and S, said ring optionally substituted with one or two groups independently selected from $CH_3$, $OCH_3$, $C(O)CH_3$, $CO_2CH_3$, $OC(O)CH_3$, CN, and halo, wherein all methyl groups are optionally substituted with 1, 2, or 3 halogen atoms; and d) with one group selected from $C_{1-6}$ alkanoyl, $C_{1-6}$ alkoxycarbonyl, $C_{1-6}$ alkylcarbamoyl, ethylcarbamoylmethyl methylcarbamoylmethyl, 2-hydroxy-2-phenyl-ethylcarbamoylmethyl, or N-phthalimido;

or $R_3$ is $R_4NHC(O)$, $R_4NHC(S)$, or $R_4NHCH_2C(O)$, wherein $R_4$ is $C_{1-6}$ alkyl, wherein said alkyl group may be straight-chain, branched, or cyclic, and is optionally substituted as described for $R_3$ alkyl groups, or $R_4$ is a five- or 6-membered aromatic ring containing 0-3 heteroatoms independently selected from O, N, and S, all $R_4$ optionally substituted with one or two substituents independently selected from halo, methyl, and benzyl, wherein all rings are optionally substituted with one or two groups independently selected from $CH_3$, $OCH_3$, $CO_2CH_3$, $OC(O)CH_3$, CN, and halo, wherein all methyl groups are optionally substituted with 1, 2, or 3 halogen atoms;

and m and n are, independently, 1 or 2, provided that m and n are not both 2;

and where formula II is

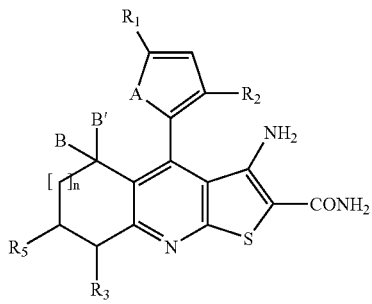

Formula II wherein n is zero, 1, 2, or 3; A is S, O, or $N(CH_3)$;

B and B' are either both H or jointly oxo;

$R_1$ and $R_2$ are, independently, H, $CH_3$, $CF_3$, or $CH_3O$;

$R_3$ is H;

or $R_3$ is a 5- or 6-membered ring, said ring optionally containing one or more double bonds, optionally containing 1-3 ring heteroatoms independently selected from O, N, and S, and optionally substituted with one or two groups independently selected from $CH_3$, $OCH_3$, $CO_2CH_3$, $OC(O)CH_3$, CN, and halo, wherein all methyl groups are optionally substituted with 1, 2, or 3 halogen atoms;

or $R_3$ is $C_{1-6}$ alkyl, $C_{1-6}$ alkanoyl, $C_{1-6}$ alkenyl, $C_{1-6}$ alkoxy, $C_{1-6}$ alkenoxy, wherein said alkyl groups, the alkyl moieties of said alkanoyl and said alkoxy groups, said alkenyl groups, and the alkenyl moieties of said alkenoxy groups may be straight-chain, branched, or cyclic, and may optionally be substituted as follows:

a) with one, two, or three halogen atoms;

b) with one or two substituents independently selected from hydroxy, carboxyl, cyano, benzyl, benzoyl, and benzoyloxy;

c) with one saturated, unsaturated, or aromatic 5- or 6-membered ring containing 0-3 heteroatoms selected from N, O, and S, said ring optionally substituted with one or two groups independently selected from $CH_3$, $OCH_3$, $C(O)CH_3$, $CO_2CH_3$, $OC(O)CH_3$, CN, and halo, wherein all methyl groups are optionally substituted with 1, 2, or 3 halogen atoms; and d) with one group selected from $C_{1-6}$ alkanoyl, $C_{1-6}$ alkoxycarbonyl, $C_{1-6}$ alkylcarbamoyl, ethylcarbamoylmethyl methylcarbamoylmethyl, 2-hydroxy-2-phenyl-ethylcarbamoylmethyl, or N-phthalimido;

or $R_3$ is $R_4NHC(O)$, $R_4NHC(S)$, or $R_4NHCH_2C(O)$, wherein $R_4$ is $C_{1-6}$ alkyl, wherein said alkyl group may be straight-chain, branched, or cyclic, and is optionally substituted as described for $R_3$ alkyl groups, or $R_4$ is a five- or 6-membered aromatic ring containing 0-3 heteroatoms independently selected from O, N, and S, all $R_4$ optionally substituted with one or two substituents independently selected from halo, methyl, and benzyl, wherein all rings are optionally substituted with one or two groups independently selected from $CH_3$, $OCH_3$, $CO_2CH_3$, $OC(O)CH_3$, CN, and halo, wherein all methyl groups are optionally substituted with 1, 2, or 3 halogen atoms; and $R_5$ is H or $C_3$ alkyl; or $R_3$ and $R_5$, together with the ring carbon atoms to which they are attached, form an additional fused 5- or 6-membered cycloalkyl group.

16. The method of claim 15, wherein a compound of formula I is administered where A is S, n is 1, m is 1, $R_1$ is H, and $R_2$ is H or $CH_3$.

17. The method of claim 16, wherein $R_3$ is H or $C_{1-6}$ alkyl, optionally substituted with one or two substituents independently selected from halo, hydroxy, cyano, phenyl, pyridyl, benzoyl, benzoyl methyl, benzoyloxy, $C_{1-6}$ alkoxycarbonyl, $C_{1-6}$ alkylcarbamoyl, N-phthalimido, or $R_3$ is a 5- or 6-membered aromatic ring containing 1-3 heteroatoms independently selected from O, N, and S, wherein all rings are optionally substituted with one or two substituents independently selected from halo, $CH_3$, $CH_3O$, CN, $CF_3$, and $CH_3C(O)$, wherein all methyl groups are optionally substituted 1-3 chlorine atoms.

18. The method of claim 17, wherein $R_3$ is $C_{1-4}$ alkyl, optionally monosubstituted with halogen, hydroxy, phenyl, benzyl, pyridyl, and pyridyl methyl, wherein the phenyl and pyridyl rings are optionally further monosubstituted with methyl or halogen.

19. The method of claim 16, wherein $R_3$ is $R_4NHC(O)$, $R_4NHC(S)$, or $R_4NHCH_2C(O)$, wherein $R_4$ is $C_{1-6}$ alkyl, wherein said alkyl group may be straight-chain, branched, or cyclic, and is optionally substituted as described for $R_3$ alkyl groups, or $R_4$ is a five- or 6-membered aromatic ring containing 0-3 heteroatoms independently selected from O, N, and S, all $R_4$ optionally substituted with one or two substituents independently selected from halo, methyl, and benzyl, wherein all rings are optionally substituted with one or two groups independently selected from $CH_3$, $OCH_3$, $CO_2CH_3$, $OC(O)CH_3$, CN, and halo, wherein all methyl groups are optionally substituted with 1, 2, or 3 halogen atoms.

20. The method of claim 15, wherein wherein a compound of formula I is provided, and A is S, n is 2, m is 1, $R_1$ is H, and $R_2$ is H or $CH_3$.

21. The method of claim 20, wherein $R_3$ is H or $C_{1-4}$ alkyl.

22. The method of claim 15, wherein a compound of formula I is administered, and A is O, n is 1, m is 1, $R_1$ is H, and $R_2$ is H or $CH_3$.

23. The method of claim 22, wherein $R_3$ is H or $C_{1-6}$ alkyl, optionally substituted with one or two substituents independently selected from halo, hydroxy, cyano, phenyl, pyridyl, benzoyl, benzoyl methyl, benzoyloxy, $C_{1-6}$ alkoxycarbonyl, $C_{1-6}$ alkylcarbamoyl, N-phthalimido, or $R_3$ is a 5- or 6-membered aromatic ring containing 1-3 heteroatoms independently selected from O, N, and S, wherein all rings are optionally substituted with one or two substituents independently selected from halo, $CH_3$, $CH_3O$, CN, $CF_3$, and $CH_3C(O)$, wherein all methyl groups are optionally substituted 1-3 chlorine atoms.

24. The method of claim 23, wherein $R_3$ is $C_{1-4}$ alkyl, optionally monosubstituted with halogen, hydroxy, phenyl, benzyl, pyridyl, and pyridyl methyl, wherein the phenyl and pyridyl rings are optionally monosubstituted with methyl or halogen.

25. The method of claim 22, wherein $R_3$ is $R_4NHC(O)$, $R_4NHC(S)$, or $R_4NHCH_2C(O)$, wherein $R_4$ is $C_{1-6}$ alkyl, wherein said alkyl group may be straight-chain, branched, or cyclic, and is optionally substituted as described for $R_3$ alkyl groups, or $R_4$ is a five- or 6-membered aromatic ring containing 0-3 heteroatoms independently selected from O, N, and S, all $R_4$ optionally substituted with one or two substituents independently selected from halo, methyl, and benzyl, wherein all rings are optionally substituted with one or two groups independently selected from $CH_3$, $OCH_3$, $CO_2CH_3$, $OC(O)CH_3$, CN, and halo, wherein all methyl groups are optionally substituted with 1, 2, or 3 halogen atoms.

26. The method claim 15, wherein a compound of formula II is administered.

27. The method of claim 26, wherein A is S, $R_5$ is H; and wherein $R_3$ is selected from H, $C_{1-4}$ alkyl, $C_{1-4}$ alkenyl, or $C_{1-6}$ alkoxy, wherein said alkyl groups, the alkyl moieties of said alkoxy groups, and said alkenyl groups may be straight-chain, branched, or cyclic, and are optionally substituted with one or two substituents independently selected from halo, hydroxy, ethylcarbamoylmethyl, methylcarbamoylmethyl, 2-hydroxy-2-phenyl-ethylcarbamoylmethyl, benzoyl, benzoyloxy, and a 5- or 6-membered ring, said ring optionally containing one or more double bonds, optionally containing 1-3 ring heteroatoms independently selected from O, N, and S, and optionally substituted with, independently, one or two groups independently selected from $CH_3$, $OCH_3$, $CF_3$, and halo; and n=0, 1, or 2.

28. The method of claim 26, wherein n=1 or 2, and $R_3$ is H, methyl, methoxy, ethoxy or allyl.

* * * * *